(12) United States Patent
Ziegler et al.

(10) Patent No.: US 8,065,924 B2
(45) Date of Patent: Nov. 29, 2011

(54) CASSETTE FOR DIFFERENTIAL PRESSURE BASED MEDICATION DELIVERY FLOW SENSOR ASSEMBLY FOR MEDICATION DELIVERY MONITORING AND METHOD OF MAKING THE SAME

(75) Inventors: John S. Ziegler, Arlington Heights, IL (US); Brian Barclay, Pleasant Prairie, WI (US); James D. Jacobson, Lindenhurst, IL (US); Michael G. Lowery, Wildwood, IL (US); Thomas D. Johnson, Gurnee, IL (US)

(73) Assignee: Hospira, Inc., Lake Forrest, IL (US)

( * ) Notice: Subject to any disclaimer, the term of this patent is extended or adjusted under 35 U.S.C. 154(b) by 179 days.

(21) Appl. No.: 12/468,994

(22) Filed: May 20, 2009

(65) Prior Publication Data
US 2009/0288497 A1 Nov. 26, 2009

Related U.S. Application Data

(60) Provisional application No. 61/055,605, filed on May 23, 2008.

(51) Int. Cl.
*G01F 1/42* (2006.01)
(52) U.S. Cl. .................................. 73/861.61
(58) Field of Classification Search ............... 73/861.52, 73/861.61; 604/67, 151
See application file for complete search history.

(56) References Cited

U.S. PATENT DOCUMENTS

| | | | |
|---|---|---|---|
| 4,195,515 A | 4/1980 | Smoll | |
| 4,240,294 A | 12/1980 | Grande | |
| 4,261,356 A | 4/1981 | Turner et al. | |
| 4,343,316 A | 8/1982 | Jespersen | |
| 4,626,244 A | 12/1986 | Reinicke | |
| 4,694,273 A | 9/1987 | Franchino | |
| 4,758,228 A | 7/1988 | Williams | |
| 4,856,339 A | 8/1989 | Williams | |
| 4,881,413 A | 11/1989 | Georgi et al. | |
| 4,892,656 A | 1/1990 | Pietzsch | |

(Continued)

FOREIGN PATENT DOCUMENTS

JP 10239193 * 11/1998

(Continued)

OTHER PUBLICATIONS

Alan F. Merry, Craig S. Webster and Daniel J. Matthew et al. A New Safety-Oriented Integrated Drug Administration and Automated Anesthesia Record System. Anesth Analg 2001;93:385-90.

(Continued)

*Primary Examiner* — Jewel V Thompson
(74) *Attorney, Agent, or Firm* — Michael R. Crabb

(57) ABSTRACT

A disposable assembly for use with a sensor assembly, and method for making the same, the disposable comprises a body, a flow restricting element, and a fluid pressure membrane. The body has a lid portion and a base portion. The body defines a fluid flow passage that forms an inlet and an outlet. The flow restricting element is positioned along the fluid flow passage between the inlet and the outlet. The fluid pressure membrane is at a location in the fluid flow passage between the inlet and the outlet. The fluid pressure membrane defines an opening for receiving the flow restricting element. The fluid pressure membrane is located between the lid portion and the base portion of the body.

29 Claims, 14 Drawing Sheets

U.S. PATENT DOCUMENTS

| | | |
|---|---|---|
| 4,938,079 A | 7/1990 | Goldberg |
| 4,947,856 A | 8/1990 | Beard |
| 5,211,626 A | 5/1993 | Frank et al. |
| 5,242,406 A | 9/1993 | Gross et al. |
| 5,287,851 A | 2/1994 | Beran et al. |
| 5,292,306 A | 3/1994 | Wynkoop et al. |
| 5,325,728 A | 7/1994 | Zimmerman et al. |
| 5,417,119 A | 5/1995 | Smoll |
| 5,417,395 A | 5/1995 | Fowler et al. |
| 5,450,758 A | 9/1995 | Smoll |
| 5,463,906 A | 11/1995 | Spani et al. |
| 5,611,784 A | 3/1997 | Barresi et al. |
| 5,628,309 A | 5/1997 | Brown |
| 5,651,775 A | 7/1997 | Walker et al. |
| 5,672,832 A | 9/1997 | Cucci et al. |
| 5,697,916 A | 12/1997 | Schraga |
| 5,728,074 A | 3/1998 | Castellano et al. |
| 5,752,918 A | 5/1998 | Fowler et al. |
| 5,758,643 A | 6/1998 | Wong et al. |
| 5,805,455 A | 9/1998 | Lipps |
| 5,848,971 A | 12/1998 | Fowler et al. |
| 5,891,051 A | 4/1999 | Han et al. |
| 5,904,666 A | 5/1999 | DeDecker et al. |
| 5,944,660 A | 8/1999 | Kimball et al. |
| 5,947,911 A | 9/1999 | Wong et al. |
| 6,032,536 A | 3/2000 | Peeters et al. |
| 6,068,615 A | 5/2000 | Brown et al. |
| 6,250,132 B1 | 6/2001 | Drzewiecki |
| 6,270,455 B1 | 8/2001 | Brown |
| 6,272,934 B1 | 8/2001 | Rajan et al. |
| 6,277,099 B1 | 8/2001 | Strowe et al. |
| 6,349,740 B1 | 2/2002 | Cho et al. |
| 6,385,505 B1 | 5/2002 | Lipps |
| 6,386,050 B1 | 5/2002 | Yin et al. |
| 6,445,053 B1 | 9/2002 | Cho |
| 6,482,185 B1 | 11/2002 | Hartmann |
| 6,558,125 B1 | 5/2003 | Futterknecht |
| 6,578,435 B2 | 6/2003 | Gould et al. |
| RE38,189 E | 7/2003 | Walker et al. |
| 6,609,047 B1 | 8/2003 | Lipps |
| D481,121 S | 10/2003 | Evans |
| D485,356 S | 1/2004 | Evans |
| 6,685,668 B1 | 2/2004 | Cho et al. |
| 6,685,678 B2 | 2/2004 | Evans et al. |
| 6,700,174 B1 | 3/2004 | Miu et al. |
| 6,760,643 B2 | 7/2004 | Lipps |
| 6,813,964 B1 | 11/2004 | Clark et al. |
| 6,920,795 B2 | 7/2005 | Bischoff et al. |
| 6,932,796 B2 | 8/2005 | Sage et al. |
| 6,935,192 B2 | 8/2005 | Sobek et al. |
| 6,964,204 B2 | 11/2005 | Clark et al. |
| 6,975,922 B2 | 12/2005 | Duncan et al. |
| 6,981,960 B2 | 1/2006 | Cho et al. |
| 7,059,184 B2 | 6/2006 | Kanoula et al. |
| 7,074,209 B2 | 7/2006 | Evans et al. |
| 7,082,843 B2 | 8/2006 | Clark et al. |
| 7,096,729 B2 | 8/2006 | Repko et al. |
| 7,115,113 B2 | 10/2006 | Evans et al. |
| 7,161,488 B2 | 1/2007 | Frasch |
| 7,162,290 B1 | 1/2007 | Levin |
| 7,162,927 B1 | 1/2007 | Selvan et al. |
| 7,415,895 B2 | 8/2008 | Kurisaki et al. |
| 7,503,903 B2 | 3/2009 | Carlisle et al. |
| 7,571,024 B2 | 8/2009 | Duncan et al. |
| 7,693,697 B2 | 4/2010 | Westenkow et al. |
| 2002/0099334 A1 | 7/2002 | Hanson et al. |
| 2002/0123741 A1 | 9/2002 | Rake et al. |
| 2003/0065537 A1 | 4/2003 | Evans |
| 2004/0082918 A1 | 4/2004 | Evans et al. |
| 2004/0225409 A1 | 11/2004 | Duncan et al. |
| 2004/0232219 A1 | 11/2004 | Fowler |
| 2004/0251406 A1 | 12/2004 | Figueria |
| 2006/0142692 A1* | 6/2006 | Jacobson et al. ............ 604/67 |
| 2006/0181695 A1 | 8/2006 | Sage, Jr. |
| 2006/0260416 A1 | 11/2006 | Sage et al. |
| 2006/0266128 A1* | 11/2006 | Clark et al. ............ 73/861.52 |
| 2007/0060872 A1 | 3/2007 | Hall et al. |
| 2007/0129618 A1 | 6/2007 | Goldberger et al. |
| 2007/0179436 A1 | 8/2007 | Braig et al. |
| 2009/0004767 A1 | 1/2009 | Parks et al. |
| 2009/0157040 A1 | 6/2009 | Jacobson et al. |
| 2010/0198155 A1 | 8/2010 | Moy et al. |

FOREIGN PATENT DOCUMENTS

| | | |
|---|---|---|
| JP | 2007071695 | 3/2007 |
| WO | 0227276 A2 | 4/2002 |
| WO | 2005082450 A1 | 9/2005 |
| WO | 2005118015 A1 | 12/2005 |

OTHER PUBLICATIONS

Dec. 2005 Advertisement from SensorONE Ltd for the Series PD-39 X Differential Pressure Transmitter.

2005 Advertisement form BARD for the CritiCore Monitor.

\* cited by examiner

CASSETTE FOR DIFFERENTIAL PRESSURE BASED MEDICATION DELIVERY FLOW SENSOR ASSEMBLY FOR MEDICATION DELIVERY MONITORING AND METHOD OF MAKING THE SAME

CROSS REFERENCE TO RELATED APPLICATIONS

This application claims priority under 35 U.S.C. 119 of U.S. Ser. No. 61/055,605 filed May 23, 2008.

TECHNICAL FIELD

The present invention generally relates to a differential pressure based flow sensor assembly and method for monitoring medication delivery utilizing a system containing the differential pressure based flow sensor assembly, and more particularly to a differential pressure based flow sensor assembly that has a disposable portion and a reusable portion. More particularly, the present invention relates to a cassette to serve as the disposable portion of such a flow sensor assembly and methods of making the same.

BACKGROUND

Modern medical devices, including medical pumps, are increasingly being controlled by microprocessor based systems to deliver fluids, solutions, medications, and drugs to patients. A typical control for a medical pump includes a user interface enabling a medical practitioner to enter the dosage of fluid to be delivered, the rate of fluid delivery, the duration, and the volume of a fluid to be infused into a patient. Typically, drug delivery is programmed to occur as a continuous infusion or as a single bolus dose.

It is common for a plurality of medications to be infused to a patient by using a multi-channel infusion pump or using a plurality of single channel infusion pumps where a different fluid is administered from each channel. Another method of delivering multiple medications to a patient is to deliver a first medication using an infusion pump, and additional medications through single bolus doses.

When delivering medications through single bolus doses it is important to verify that correct medications are being delivered to the patient as well to verify that the correct amount of medication is being delivered to the patient. Typically a caregiver simply manually notes on the patient's paper chart the amount of medication delivered via a bolus dose, and that information may later be entered into a patient's record electronically. Thus, human error may lead to an accidental overdose or underdose of a medication, while a caregiver believes that a proper dose was delivered. In addition to an error in medication dosing, it is also possible that human error may result in the failure to record the medication delivered during a single bolus dose. Thus, it is possible that a patient's medical records may not reflect every medication that patient has been given. A sensor within the IV line capable of measuring a wide range of fluids and flow rates would be helpful in documenting the flow rate and volume of every medication the patient is given through that line. Further, it is desirable to provide a robust flow rate sensing methodology that is low cost and in particular introduces low incremental cost to the disposable medication delivery tubing set. Further, it is desirable to provide a flow rate sensing methodology that is capable of accurately sensing the flow rate of fluids that have a range of physical properties, including fluid viscosity, which may not be known precisely. Therefore, a need exists for a differential pressure based flow sensor system adapted for monitoring medication delivery.

SUMMARY

According to one embodiment, a differential pressure based flow sensor assembly adapted to determine the rate of a fluid system comprises a disposable portion, and a reusable portion. The disposable portion has a body that defines a fluid flow passage that forms an inlet and an outlet. A flow restricting element is positioned along the fluid flow passage between the inlet and the outlet. The disposable portion further has an upstream fluid pressure membrane at a location within the fluid flow passage between the inlet and the flow restricting element. A downstream fluid pressure membrane is located in the fluid flow passage between the flow restricting element and the outlet of the disposable portion.

The reusable portion has an upstream fluid pressure sensor and a downstream fluid pressure sensor. The upstream fluid pressure sensor senses the upstream fluid pressure at a location within the fluid flow passage between the inlet and the flow restricting element. The upstream fluid pressure sensor is positioned to determine the fluid pressure at the upstream fluid pressure membrane.

The downstream fluid pressure sensor senses the downstream fluid pressure at a location within the fluid flow passage between the flow restricting element and the outlet. The downstream fluid pressure sensor is positioned to determine the fluid pressure at the downstream fluid pressure membrane.

According to another embodiment, a disposable assembly for use with a differential pressure based fluid flow assembly comprises a body, a flow restricting element, an upstream fluid pressure membrane, and a downstream fluid pressure membrane. The body defines a fluid flow passage that forms an inlet and an outlet. The flow restricting element is positioned between the inlet and the outlet within the fluid flow passage. The upstream fluid pressure membrane is located within the fluid flow path between the inlet and the flow restricting element. The downstream fluid pressure membrane is located within the fluid flow path between the flow restricting element and the outlet.

According to one method, a fluid flow rate in a fluid flow system is determined. The method provides a differential pressure based flow sensor assembly. The sensor assembly comprises a disposable portion, and a reusable portion. The disposable portion has a body that defines a fluid flow passage that forms an inlet and an outlet. A flow restricting element is positioned along the fluid flow passage between the inlet and the outlet. The disposable portion further has an upstream fluid pressure membrane at a location within the fluid flow passage between the inlet and the flow restricting element. A downstream fluid pressure membrane is located in the fluid flow passage between the flow restricting element and the outlet of the disposable portion. The reusable portion has an upstream fluid pressure sensor and a downstream fluid pressure sensor.

The upstream fluid pressure sensor senses the upstream fluid pressure at a location within the fluid flow passage between the inlet and the flow restricting element. The upstream fluid pressure sensor is positioned to determine the fluid pressure at the upstream fluid pressure membrane. The downstream fluid pressure sensor senses the downstream fluid pressure at a location within the fluid flow passage between the flow restricting element and the outlet.

The downstream fluid pressure sensor is positioned to determine the fluid pressure at the downstream fluid pressure membrane. Fluid is directed through the fluid flow passage. The process calculates the fluid flow rate based on a pressure difference between an output of the upstream fluid pressure sensor and an output of the downstream fluid pressure sensor.

According to a further embodiment, a fluid delivery system for delivering the fluid medication from a first source to a patient, and for measuring the flow rate of the fluid, comprises an infusion pump, a differential pressure based flow sensor assembly, and a processor. The infusion pump selectively varies a rate of flow of the first medication from the first source through a fluid line. The differential pressure based flow sensor assembly determines the flow rate of the first medication within the fluid line.

The sensor assembly has a disposable portion, and a reusable portion. The disposable portion has a body that defines a fluid flow passage that forms an inlet and an outlet. A flow restricting element is positioned along the fluid flow passage between the inlet and the outlet. The disposable portion further has an upstream fluid pressure membrane at a location within the fluid flow passage between the inlet and the flow restricting element. A downstream fluid pressure membrane is located in the fluid flow passage between the flow restricting element and the outlet of the disposable portion.

The reusable portion has an upstream fluid pressure sensor and a downstream fluid pressure sensor. The upstream fluid pressure sensor senses the upstream fluid pressure at a location within the fluid flow passage between the inlet and the flow restricting element. The upstream fluid pressure sensor is positioned to determine the fluid pressure at the upstream fluid pressure membrane.

The downstream fluid pressure sensor senses the downstream fluid pressure at a location within the fluid flow passage between the flow restricting element and the outlet. The downstream fluid pressure sensor is positioned to determine the fluid pressure at the downstream fluid pressure membrane.

The processor is adapted to control the infusion pump by varying the rate of flow of the first medication based on information provided by the differential pressure based flow sensor assembly. The processor is also adapted to determine the amount of the first medication provided to the patient.

Yet another process delivers medication to a patient using a differential pressure based flow sensor assembly to determine the flow rate of a first medication within a fluid line. The sensor assembly comprises a disposable portion, and a reusable portion. The disposable portion has a body that defines a fluid flow passage that forms an inlet and an outlet. A flow restricting element is positioned along the fluid flow passage between the inlet and the outlet. The disposable portion further has an upstream fluid pressure membrane at a location within the fluid flow passage between the inlet and the flow restricting element. A downstream fluid pressure membrane is located in the fluid flow passage between the flow restricting element and the outlet of the disposable portion.

The reusable portion has an upstream fluid pressure sensor and a downstream fluid pressure sensor. The upstream fluid pressure sensor senses the upstream fluid pressure at a location within the fluid flow passage between the inlet and the flow restricting element. The upstream fluid pressure sensor is positioned to determine the fluid pressure at the upstream fluid pressure membrane. The downstream fluid pressure sensor senses the downstream fluid pressure at a location within the fluid flow passage between the flow restricting element and the outlet. The downstream fluid pressure sensor is positioned to determine the fluid pressure at the downstream fluid pressure membrane.

The process senses the flow rate of the first medication with the flow sensor assembly. An infusion pump that selectively varies the flow rate of the first medication is controlled based upon information that the flow sensor assembly provides to a processor. The process determines the amount of the first medication delivered to the patient, based upon information the flow sensor assembly provides to the processor.

A further process determines a fluid flow rate within a fluid flow system. An upstream pressure sensor is provided in a fluid flow path. A downstream pressure sensor is also provided in the fluid flow path. The process provides a flow restricting element along the fluid flow path between the upstream pressure sensor and the downstream pressure sensor. Fluid is directed through the fluid flow path. A fluid flow rate is calculated based upon the pressure difference between an output of the upstream fluid pressure sensor and an output of the downstream fluid pressure sensor.

According to another embodiment, a differential pressure based flow sensor assembly to determine the flow rate of a fluid system comprises a disposable portion and a reusable portion. The disposable portion has a body, a fluid pressure membrane, and a flow restricting element. The body defines a fluid flow passage that forms an inlet and an outlet. The body has a base portion and a lid portion. The fluid pressure membrane is located in the fluid flow passage between the inlet and the outlet. The fluid pressure membrane is positioned between the base portion and the lid portion of the body. The flow restricting element is positioned along the fluid flow passage between the inlet and the outlet. The fluid pressure membrane defines an opening for receiving the flow restricting element. The reusable portion has an upstream fluid pressure sensor and a downstream fluid pressure sensor. The upstream fluid pressure sensor senses an upstream fluid pressure at an upstream location in the fluid flow passage between the inlet and the flow restricting element. The downstream fluid pressure sensor senses a downstream fluid pressure at a downstream location in the fluid flow passage between the flow restricting element and the outlet.

According to still yet another embodiment, a disposable assembly for use with a sensor assembly comprises a body, a flow restricting element, and a fluid pressure membrane. The body has a lid portion and a base portion. The body defines a fluid flow passage that forms an inlet and an outlet. The flow restricting element is positioned along the fluid flow passage between the inlet and the outlet. The fluid pressure membrane is at a location in the fluid flow passage between the inlet and the outlet. The fluid pressure membrane defines an opening for receiving the flow restricting element.

According to another method a disposable assembly for use with a differential pressure based fluid flow sensor assembly is formed. The method provides a base portion and a lid portion. A flow restricting element is inserted into a fluid pressure membrane. The fluid pressure membrane defines an opening to receive the flow restricting element. The fluid pressure membrane is positioned within the base portion. The method places the lid portion adjacent the base portion, such that fluid pressure membrane is between the lid portion and base portion. The lid portion is secured to the base portion.

DETAILED DESCRIPTION

Figure 1:
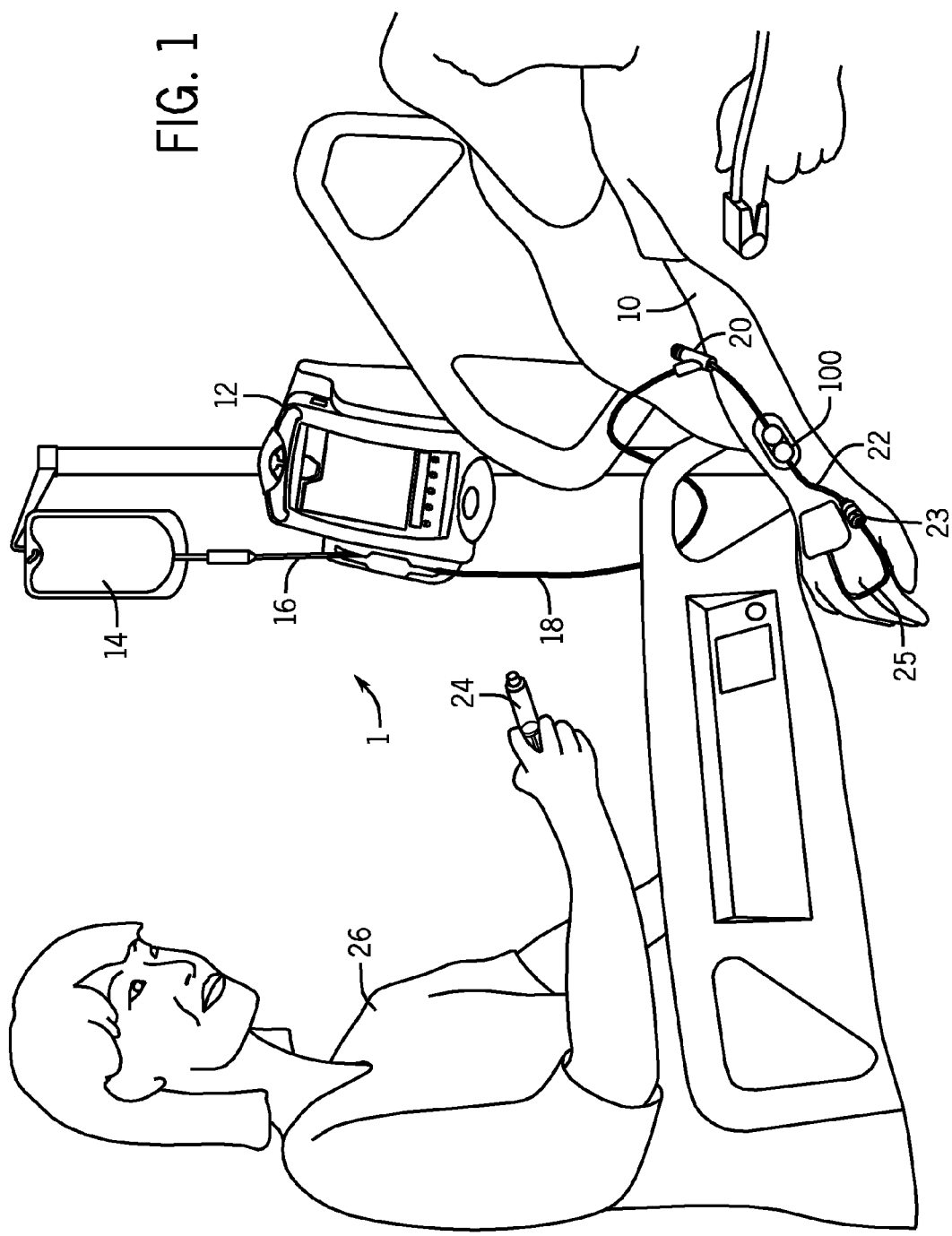
FIG. 1 is a pictorial view that illustrates a patient connected to IV line having a differential pressure based flow sensor assembly according to one embodiment.

While this invention is susceptible of embodiments in many different forms, there is shown in the drawings and will herein be described an example of the invention. The present disclosure is to be considered as an example of the principles of the invention. It is not intended to limit the broad aspect of the invention to the examples illustrated.

FIG. 1 is a pictorial representation of a patient 10 connected to a medication delivery system 1 and receiving a first medication via an infusion pump 12 from a medication reservoir 14. A first fluid line segment 16 delivers the first medication from the reservoir 14 to the infusion pump 12. The second fluid line segment 18 delivers the medication from the infusion pump 12 to a differential pressure based flow sensor assembly 100. A third fluid line segment 22 delivers the medication from the differential pressure based flow sensor 100 to the patient 10. While three fluid lines segments are described in connection with FIG. 1, it is contemplated that the number of fluid lines or line segments used in connection with the present invention may vary, and may be more or less than three fluid lines. The third fluid line segment 22 is typically connected to the patient 10 through a connector valve 23 and a patient access device such as a catheter 25.

The second fluid line segment 18 has a connection 20 adapted to receive a second medication from a second source. The connection illustrated in FIG. 1 is typically referred to as a Y-Site, although it is contemplated that other connection types and configurations may be used in connection with the present invention.

Figure 2:
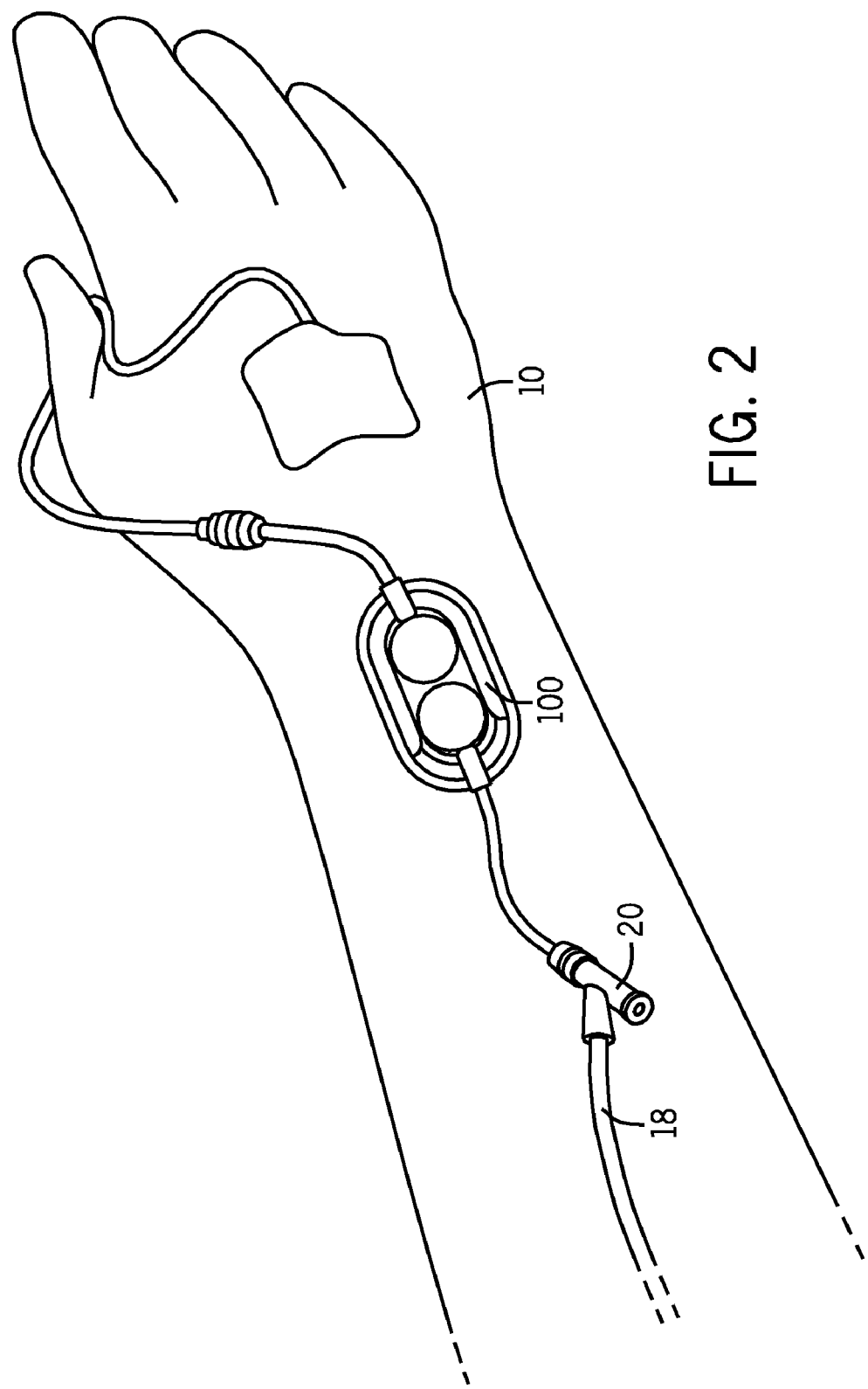
FIG. 2 shows a closer, more detailed pictorial view of the differential pressure based flow sensor assembly of the embodiment of FIG. 1.
Figure 6:
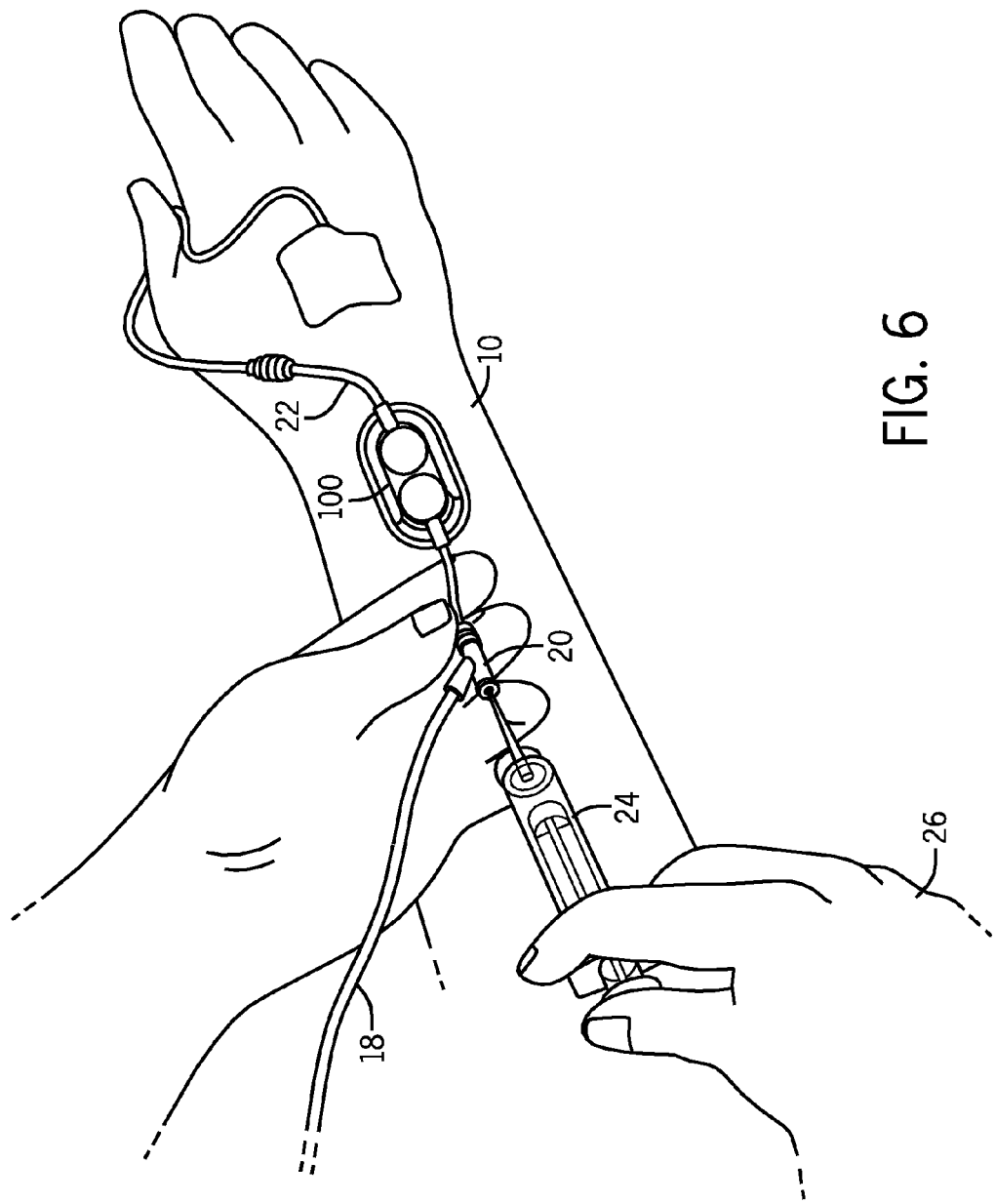
FIG. 6 is a pictorial view illustrating delivery of medication to a patient via an IV push or bolus through an IV line having the differential pressure based flow sensor assembly of FIG. 1.

The connection 20, shown in additional detail in FIG. 2, may receive a second medication from a syringe 24 in the form of a manual IV push or bolus by a caregiver 26 (see FIG. 6). It is further contemplated that the second medication may be provided in another fashion, such as from a second medication reservoir or other known medication delivery source. The medication delivery system 1 further has a differential pressure based flow sensor assembly 100. In the illustrated embodiment, the differential pressure based flow sensor assembly 100 is located downstream of the connector 20 and is secured on the patient 10. Thus, the flow sensor assembly is adapted to have both the first and the second medication pass through the sensor assembly 100. However, the sensor assembly 100 could also be disposed in any number of locations including but not limited to upstream of the fluid junction between the first and second medication, connected between the second source and the connector 20, or integrally formed on or within one of the branches of the connector 20. The flow sensor assembly 100 need not be secured to the patient 10 directly.

Figure 3:
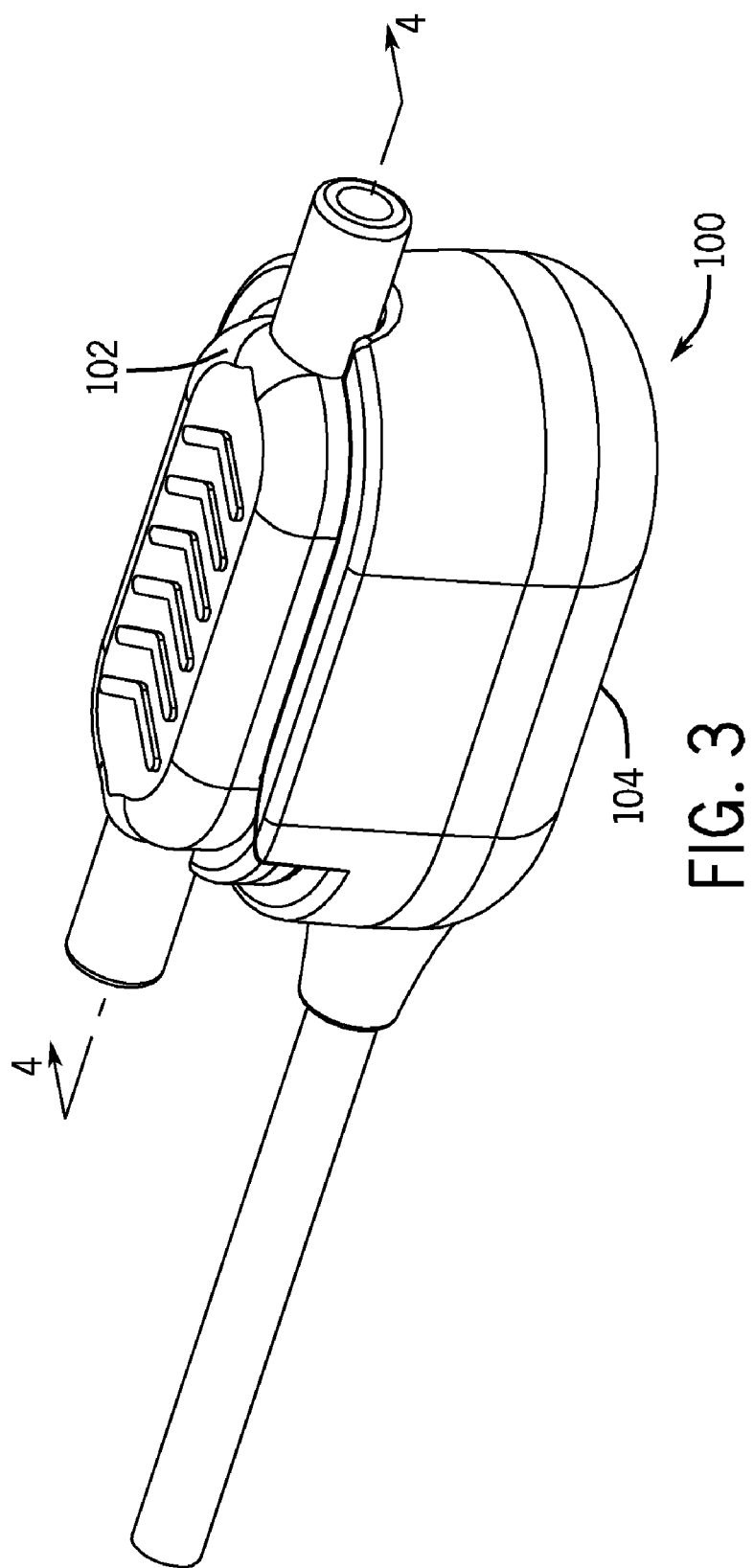
FIG. 3 is an isometric view of a differential pressure based flow sensor assembly of the embodiment of FIG. 1.
Figure 4:
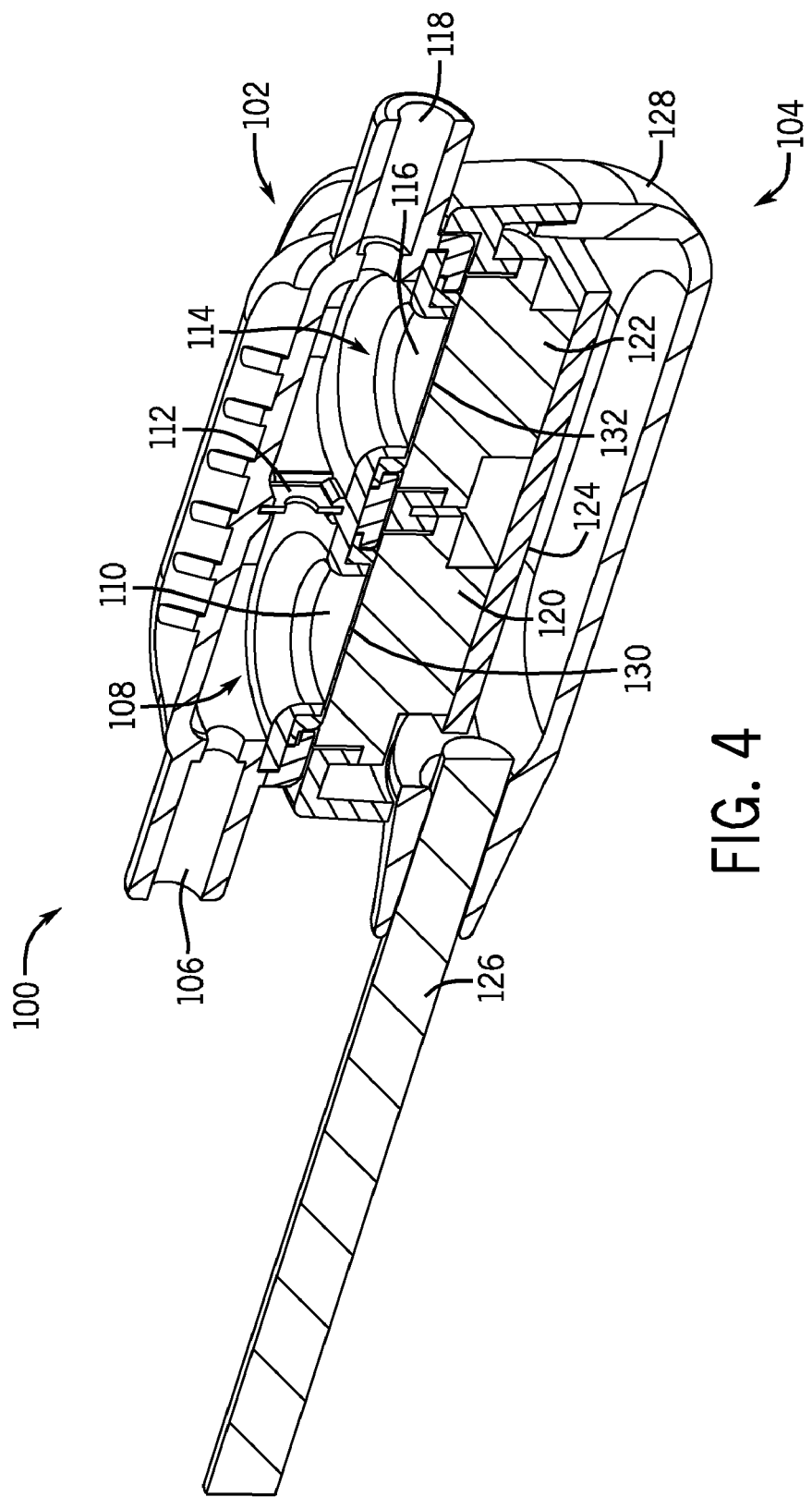
FIG. 4 is a cross-sectional view taken along line 4-4 of FIG. 3.

Turning next to FIG. 3 and FIG. 4, the differential pressure based flow sensor assembly 100 is shown in additional detail. The differential pressure based flow sensor assembly 100 has a disposable portion 102 and a reusable portion 104. As used herein reusable is defined as a component that is capable of being safely reused. For example, the same reusable portion 104 can be used multiple times on the same patient with the disposable portion 102 being changed at least every 72 hours or so. The same reusable portion 104 can be used hundreds or even thousands of times on different patients, subject to the cleaning policies recommended by the manufacturer or the healthcare institution, by installing a new disposable portion 102. This is possible since the reusable portion 104 is designed to prevent fluid ingress. As may best be seen in FIG. 4, the disposable portion 102 has a fluid inlet 106, an upstream fluid chamber 108, an upstream fluid pressure membrane 110, a flow restricting element 112, a downstream fluid chamber 114, a downstream fluid pressure membrane 116, and a fluid outlet 118. The membranes 110 and 116 are fluid impermeable. Although full membranes are shown, it is contemplated that other types of seals, including but not limited to one or more gaskets and O-rings, would suffice to keep fluid out of the housing of the reusable portion. Any exposed areas could be swabbed with a cleaning solution, if necessary.

As shown in FIG. 4, medication enters the disposable portion 102 through the fluid inlet 106. The medication flows into the upstream fluid chamber 108 from the fluid inlet 106. Next, the medication flows through the flow restricting element 112 and into the downstream fluid chamber 114. The flow of the medication through the flow restricting element 112 results in a drop in fluid pressure as the fluid flows from the upstream fluid chamber 108 to the downstream fluid chamber 114 through the flow restricting element 112. Thus, during forward fluid flow under normal conditions, the fluid pressure within the upstream fluid chamber 108 is generally greater the fluid pressure within the downstream fluid chamber 114. The fluid pressure within the upstream fluid chamber 108 presses against the upstream fluid pressure membrane 110. Similarly, the fluid pressure within the downstream fluid chamber 114 presses against the downstream fluid pressure membrane 116.

It is contemplated that a variety of materials may be utilized for the manufacture of the disposable portion 102. The disposable portion 102 may comprise a thermoplastic. It is contemplated that the flow restricting element 112 may be made of the same thermoplastic as the rest of the disposable portion 102, or may be a different material than the disposable portion 102. Non-limiting examples of the material that may be utilized to form the flow restricting element 112 include silicon, glass, and medical grade thermoplastics and elastomers. The fluid pressure membranes 110, 116 may comprise a variety of polymeric or elastomeric materials, such as TPE, or silicone.

It is additionally contemplated that the flow restricting element 112 may be formed integrally with the rest of the disposable portion 102, or the flow restricting element 112 may be a separate component placed within the disposable portion 102 as discussed below.

As may also be seen in FIG. 4, the reusable portion 104 of the differential pressure based flow rate sensor assembly 100 has an upstream pressure sensor 120, a downstream pressure sensor 122, a circuit board 124, and an electrical connection 126, all contained within a housing 128. The upstream pressure sensor 120 is adapted to interact with the upstream fluid pressure membrane 110 to generate a reading of fluid pressure within the upstream fluid chamber 108. Similarly, the downstream pressure sensor 122 is adapted to interact with the downstream fluid pressure membrane 116 to generate a reading of fluid pressure within the downstream fluid chamber 114. The circuit board 124 receives output from both the upstream pressure sensor 120 and the downstream pressure sensor 122. The circuit board 124 may calculate a pressure difference between the upstream fluid chamber 108 and the downstream fluid chamber 114, or the circuit board 126 may generate an output signal that is transmitted to another device with a processor, such as the infusion pump 12, that calculates the pressure difference between the upstream chamber 108 and the downstream chamber 114. Output of the circuit board 124 passes through electrical connection 126 to the infusion pump 12 (FIG. 1).

Although a wired electrical connection 126 is shown in FIG. 4, the system may optionally comprise wireless electrical connection and communication with the infusion pump 12 or other system components. It is additionally contemplated that according to some alternative embodiments, the reusable portion 104 may further contain additional electronics, such as, batteries, one or more memories, amplifiers, signal conditioning components, analog-to-digital converters, power converters, LED indicators, a display, sound generating components, a wireless communication engine, inductive coils for receiving power from the infusion pump 12 or another source, and active or passive radio frequency identification devices (RFID). It will be appreciated that the calculations and processing described herein can take place on the circuit board 124, in the infusion pump 12, in a remote processor (not shown), or be concentrated in only one of the system components, or distributed among one or more of the system components as needed or desired.

The components of the reusable portion 104 are contained within the housing 128. The housing 128 may be manufactured from a polymeric material such as polycarbonate, polyethylene, polyurethane, polypropylene, acrylic, or other known materials. It is further contemplated that an upstream reusable portion membrane 130 may separate the upstream fluid pressure membrane 110 from the upstream fluid pressure sensor 120. Likewise, a downstream reusable portion membrane 132 may separate the downstream fluid pressure membrane 116 from the downstream fluid pressure sensor 122.

Figure 5A:
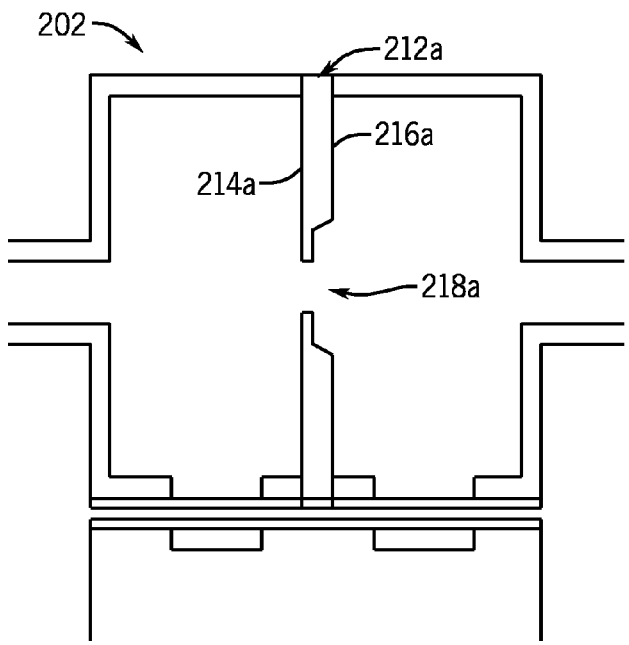
FIGS. 5a-5e illustrate cross-sections of flow restricting elements within differential pressure based flow sensor assemblies according to various embodiments.
Figures 5B, 5C, 5D, 5E:
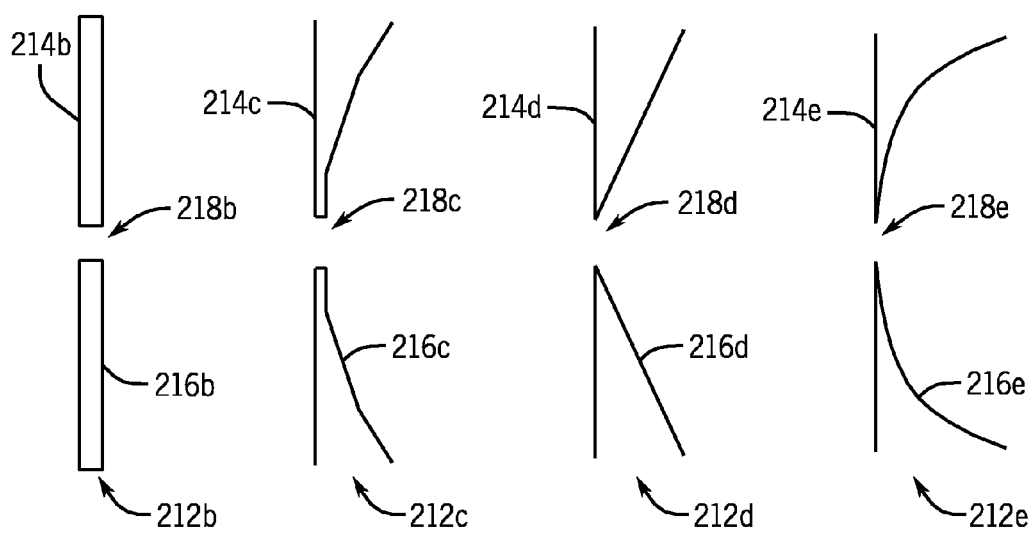

Referring next to FIG. 5a, a cross-section of a disposable portion 202 is schematically illustrated with a flow restricting element 212a to illustrate the profile of the flow restricting element 212a. The flow restricting element 212a may be identical to the flow restricting element 112, but may also vary. The flow restricting element 212a is in the form of an orifice. An orifice may be a beneficial flow restricting element, as orifice performance varies less between fluids of different viscosities than other flow restricting elements, such as capillary channels. That is to say, the measured pressure differential across an orifice for a given flow rate will be largely independent of the viscosity of the active solution, where the pressure difference measured across alternate restrictions such as capillaries will demonstrate a strong dependence upon fluid viscosity. The flow restricting element 212a has a front face 214a located on an upstream side of the flow restricting element 212a, and a rear face 216a on the downstream side of the flow restricting element 212a. An opening 218a is formed through the flow restricting element 212a to allow fluid to flow through the flow restricting element 212a.

The opening 218a may have a variety of cross-sectional shapes, but a circular opening is commonly used. In order to help reduce the effect of fluid viscosity on the flow of the fluid through the opening 218a of the flow restricting element 212a, the opening 218a may have a ratio of a perimeter of the opening 218a to the length the fluid travels though the opening 218a of from about 100:1 to about 2000:1. That is, the perimeter of the opening is sufficiently larger than the length of fluid flow though the opening 218a, such that the pressure drop through the opening 218a is less dependent on the fluid, and more dependent on the geometry of the opening 218a. An opening 218a having a perimeter to flow length ratio of about 1000:1 has been found to be effective. For example, a 430 micron diameter circular orifice with a length in the flow dimension of 12 microns will accommodate flow rates in the hundreds to thousands of ml/hr. A smaller diameter orifice would be needed for smaller flow rates and applications.

The thickness of the opening 218a of the flow restricting element may vary from about 5 microns to about 25 microns. An opening 218a having a thickness of about 12 microns has been found to be effective. In order to demonstrate the desired flow characteristics, it is important to provide a flow orifice or opening in a solid geometry. The ratio of the inlet height to the effective hydraulic diameter of the orifice should be rather large, such as at least 10:4 or about 5:1. However, a constant-thickness membrane, of thickness equal to the length of the desired orifice, may become mechanically weak if the overall area of the membrane is large. Once the orifice opening is established, the membrane material in which the orifice resides can be thicker as one moves away from the orifice perimeter. As a result, the orifice itself can provide the desired restrictive fluid path length, while the membrane in which the orifice resides is thicker than the length of the orifice at a location away from the orifice. Thus, it is contemplated that various other geometries may also be used to form a flow restricting element.

As shown in FIG. 5a, the flow restricting element 212a transitions from a thicker cross sectional shape to a thinner cross sectional shape near the opening 218a. Creating such geometry for the flow restricting element 212a allows for various low cost manufacturing approaches for the flow restricting element 212a. Creating such geometry has a limited effect on performance of the flow restricting element 212a, as such geometry does not introduce a significant pressure difference for fluids having different viscosities, but having the same fluid flow rate. Thus, the thinness of the flow restricting element 212a near the opening 218a limits the effect of fluid viscosity on pressure drop through the opening 218a, while thicker material away from the opening 218a increases the overall strength of the flow restricting element 212a.

FIGS. 5b-5e illustrate alternative flow restricting elements 212b-212e that function similarly to flow restricting element 212a. Flow restricting element 212b maintains a constant thickness, while flow restricting elements 212c-212e are thinner near the openings 218c-218e. The geometry of the rear face 216a-216e does not have a great effect on flow characteristics through openings 218a-218e. This is because flow through the opening 218a-218e typically features well-defined fluid velocity profiles with minimal fluid/wall dynamic interaction on the orifice backside, as long as the rear face 216a-216e geometry is sloped away from the orifice appropriately, and therefore minimizes viscosity induced pressure losses. Some of these orifice geometries lend themselves to manufacturing advantages. For example, orifice 218a can be formed efficiently via silicon processing techniques such as etching, lithography, masking and other MEMS operations. Orifice 218b can be formed efficiently by laser machining thin flat stock material. Orifices 218c and 218d could be formed easily with photo-imaging glass processing techniques. Orifices 218c, 218d, and 218e could be formed using molding or embossing techniques. Further combinations of techniques could be utilized within the scope of the invention.

While many embodiments have been described in connection with an upstream pressure sensor, a flow restricting element, and a downstream pressure sensor within a common assembly, it is further contemplated according to a further alternative embodiment, that these components may be separate standalone components within a fluid flow system. The methods and processes of measuring fluid flow rates and the volume of fluid flow are generally identical to those previously described according to this alternative embodiment. Thus, by monitoring the difference in pressure between a standalone upstream pressure sensor and a standalone downstream pressure sensor generated by fluid flowing through a standalone flow restricting element, the fluid flow rate may be calculated.

Turning next to FIG. 6, an IV push or bolus is shown being delivered to the patient 10. The caregiver 26 connects the syringe 24 to the second fluid line 18 via the connection 20. The caregiver 26 then delivers the mediation within the syringe 24 to the patient through the connection 20. The medication passes through the differential pressure based fluid flow sensor 100 and the third fluid line 22 to the patient 10. The differential pressure based fluid sensor assembly 100 monitors the flow rate of the medication through the sensor assembly 100. By monitoring the flow rate through the sensor assembly 100, the volume of medication delivered to the patient 10 may be calculated.

The flow rate of the fluid through the pressure sensor assembly 100 may be calculated by the following equation:

$$Q = AC_D \sqrt{\frac{2\Delta P}{\rho}},$$

where Q is the volumetric flow rate, $\Delta P$ is the pressure differential between an upstream pressure sensor and a downstream pressure sensor, $\rho$ is the fluid mass density, $C_D$ is an opening discharge coefficient, and A is the area of the opening. The use of an orifice for the opening has been empirically shown to minimize the dependence of the induced pressure differential on fluid viscosity, and the discharge coefficient remains essentially constant, thus making the flow rate a function of pressure, density, and area.

Once the flow rate Q has been calculated, the volume of the flow may be determined by integrating the flow rate over a period of time using the following equation: $V = \int Q dt$. Using this equation, both forward and backward flow thorough the sensor assembly 100 may be calculated. A negative flow rate would indicate that the pressure at the downstream sensor 122 is higher than the pressure at the upstream sensor 120, and thus fluid is flowing backwards through the sensor assembly 100, away from the patient 10.

In order to provide a more accurate $\Delta P$, a pressure tare, or calibration of the sensors, may be performed, preferably in a zero flow condition. A pressure tare subtracts the average pressure of both the upstream pressure sensor 120 and the downstream pressure sensor 122 from the readings of the respective upstream and downstream pressure sensors 120, 122 during fluid delivery. Utilizing such a pressure tare reduces the occurrence of signal drifts from pressure supply drifts, amplification, temperature variance, or residual pressures from any priming steps prior to delivering and recording a bolus dose.

Reverse flow of fluid through the sensor can be also measured with $\Delta P$ being negative. In this case, the flow is computed by taking the absolute value of $\Delta P$ and moving the negative sign outside the square root, $$Q = -AC_D \sqrt{\frac{2|\Delta P|}{\rho}}.$$

Negative flow rates are important to aggregate in the computation of true net forward volume delivery from the syringe, as they may impact the accuracy of total net volume delivered from the syringe. Additionally, an occlusion condition (i.e., the catheter 25 or the patient's vein being closed or occluded) can be detected using a back draw of the syringe prior to forward fluid delivery, a typical clinical practice. Under normal conditions, reverse flow of the fluid can be directly measured and aggregated into the net forward volume delivery. However, under occlusion scenarios, the occluded reverse flow can be quickly detected by the sensor using threshold negative limits of the downstream and upstream sensors drawing a negative vacuum pressure.

The outputs of the upstream pressure sensor 120 and the downstream pressure sensor 122 may further be monitored for detection of motion artifacts to distinguish such artifacts from true flow patterns. To detect motion artifacts, a ratio of the upstream pressure sensor 120 output to the downstream pressure sensor 122 output is monitored. If, for example, the ratio is less than a predetermined threshold, such as 3:1, it is likely that any changes in pressure indicated by the upstream pressure sensor 120 and the downstream pressure sensor 122 are the results of motion artifacts within the sensor assembly 100, not forward fluid flow. Thus, flow is only indicated when the ratio of the pressures indicated by the upstream pressure sensor 120 and the downstream pressure sensor 122 is greater than a threshold amount. This is because once flow is initiated, the flow restricting element 112 causes the pressure at the upstream pressure sensor 120 to be significantly higher than the pressure at the downstream pressure sensor 122. Alternatively, reverse fluid flow is similarly distinguished from motion artifacts, if the ratio of the downstream pressure sensor to the upstream pressure sensor is less than a limit threshold, such as 3:1, and otherwise the signal is considered motion artifacts. Pressure values obtained due to motion artifacts may be excluded from the flow rates and aggregate volume computation. Motion artifacts events are also distinguished from events indicating the true onset of flow, which is used to gate or determine the start of bolus delivery via the syringe 24.

Algorithms also are contemplated to detect the start and end of a single bolus dose. Such an algorithm may rely on a first derivative and a short term mean value of the flow rate. If the mean value of the flow rate is above a certain threshold, such as for example 300 ml/hr, and the mean value of the derivative of the flow rate is above another threshold value, such as 50 (ml/hr)/sec, this flow rate and flow rate derivative indicate a start of a bolus dose. The threshold values are selected based upon the finding that typical bolus dose deliveries have a flow rate between about 300 ml/hr to about 5000 ml/hr, while a human injecting a bolus dose is typically incapable of delivering the injection at a rate less than about 50 ml/hr, on a per second basis.

The outputs of the differential pressure sensor assembly 100 may also be used to monitor both the delivery of medication via a single bolus dose, and via an infusion pump. Such an algorithm would indicate that a flow rate below a threshold level, such as for example 300 ml/hr, is not from a bolus dose. Similarly, infusion pump cycles provide a consistent sinusoidal pattern of deliveries with every pumping cycle. Utilizing an approach that analyzes the output of the sensor assembly 100 in a frequency domain, such as through a Fourier transform, pump infusion cycles appear at a much higher frequency than flow rates introduced through a single bolus dose. A low pass filter with a cutoff frequency separating the frequency band due to an infusion pump action, versus manual delivery via a single bolus dose, can segregate the flow rate signal due to each source. Alternatively, an inverse Fourier transform of the frequencies in the band below the frequencies affected by the pump action can recover a time domain flow rate signal from the differential pressure based sensor assembly 100 to quantify the amount of flow from a single bolus dose. Such an algorithm to isolate flow due to a pump source from flow due to manual injection could also be utilized to verify an infusion pump flow rate. Similarly, pressure pulsations occurring as a result of arterial pulsations when the sensor is in direct fluidic connection with an arterial vessel can be detected and mathematically compensated for using frequency domain low pass filtering below a cutoff frequency, since manual injections are usually lower frequency than arterial pulsations. Alternatively, linear weighted averaging of pressure values measured at the sensor is a form of filtering or smoothing that can be applied on the signal to reduce the effect of pulsations. Typical infusion pumps do not measure flow volume, but rather estimate flow volume based upon pump fluidic displacement. Thus, a differential pressure based flow sensor assembly 100 may verify infusion pump function, or be used in a closed feedback loop to control pump flow rate.

Yet another algorithm contemplated allows the differential pressure based sensor assembly 100 to be used to detect air pockets within fluids flowing through the sensor assembly 100. An air pocket typically is much less dense than a fluid passing through the sensor assembly 100. Thus, an air pocket or bubble within a fluid medium generates an abrupt change in pressure value, followed by a return to expected levels. The start and end of the abrupt change in pressure values is detected by monitoring the first derivative and the second derivative of the output of the upstream pressure sensor 120 and the downstream pressure sensor 122. An abrupt change in pressure would first be noticed on the upstream pressure sensor 120, followed by an abrupt change in pressure on the downstream pressure sensor 122. These pressure changes would be followed by an abrupt resumption back to pressure levels prior to air pocket reception, once the air pocket is passed. The duration of the deviation from typical pressures is indicative of the size of the air pocket.

Figure 7:
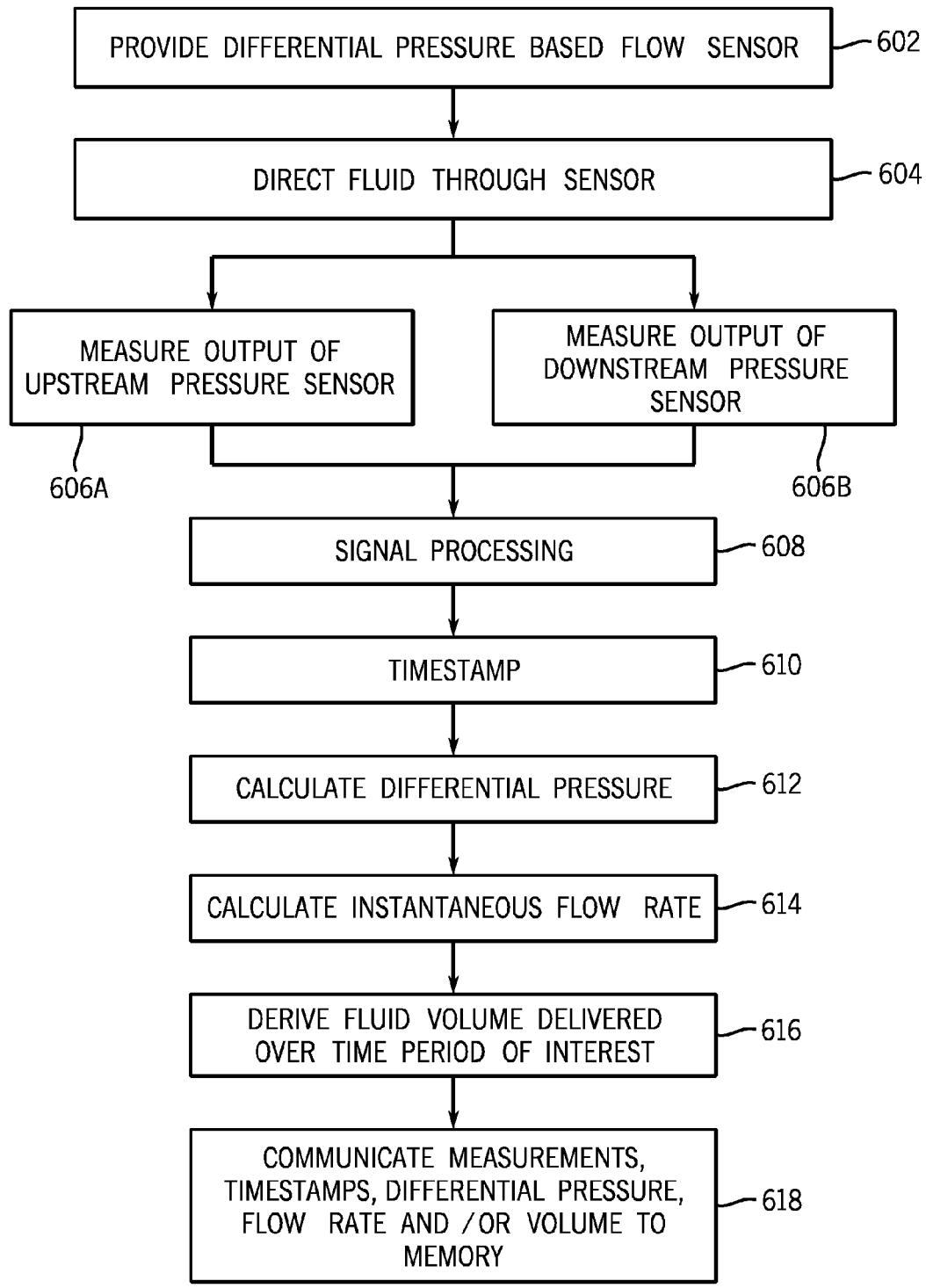
FIG. 7 schematically illustrates a method of delivering medication using a system having a differential pressure based flow sensor assembly according to one basic process.

FIG. 7 shows a basic process of utilizing a differential pressure based sensor assembly 100 to determine the instantaneous flow rate and/or volume of a fluid flow delivered through a bolus or other delivery. The process provides a differential pressure based flow sensor assembly 100 in step 602. Fluid flows through the sensor assembly in step 604. The output of the upstream pressure sensor 120 is measured in step 606A, and the output of the downstream pressure sensor 122 is measured in step 606B. The signals from the sensors 120, 122 can be filtered, amplified, or otherwise processed (for example as described above) in step 608. A timestamp is associated with the measurements in step 610. A differential pressure is calculated based upon the observed measurements in step 612. The instantaneous fluid flow rate is calculated in step 614. The flow rate is integrated over time to derive the volume deliver during the time period of interest in step 616. In step 618, the sensor signals or measurements, timestamp information, differential pressure, flow rate and/or volume delivered are communicated to a memory, which can be located in the sensor assembly 100, in the infusion pump 12, or another computer.

Figure 7A:
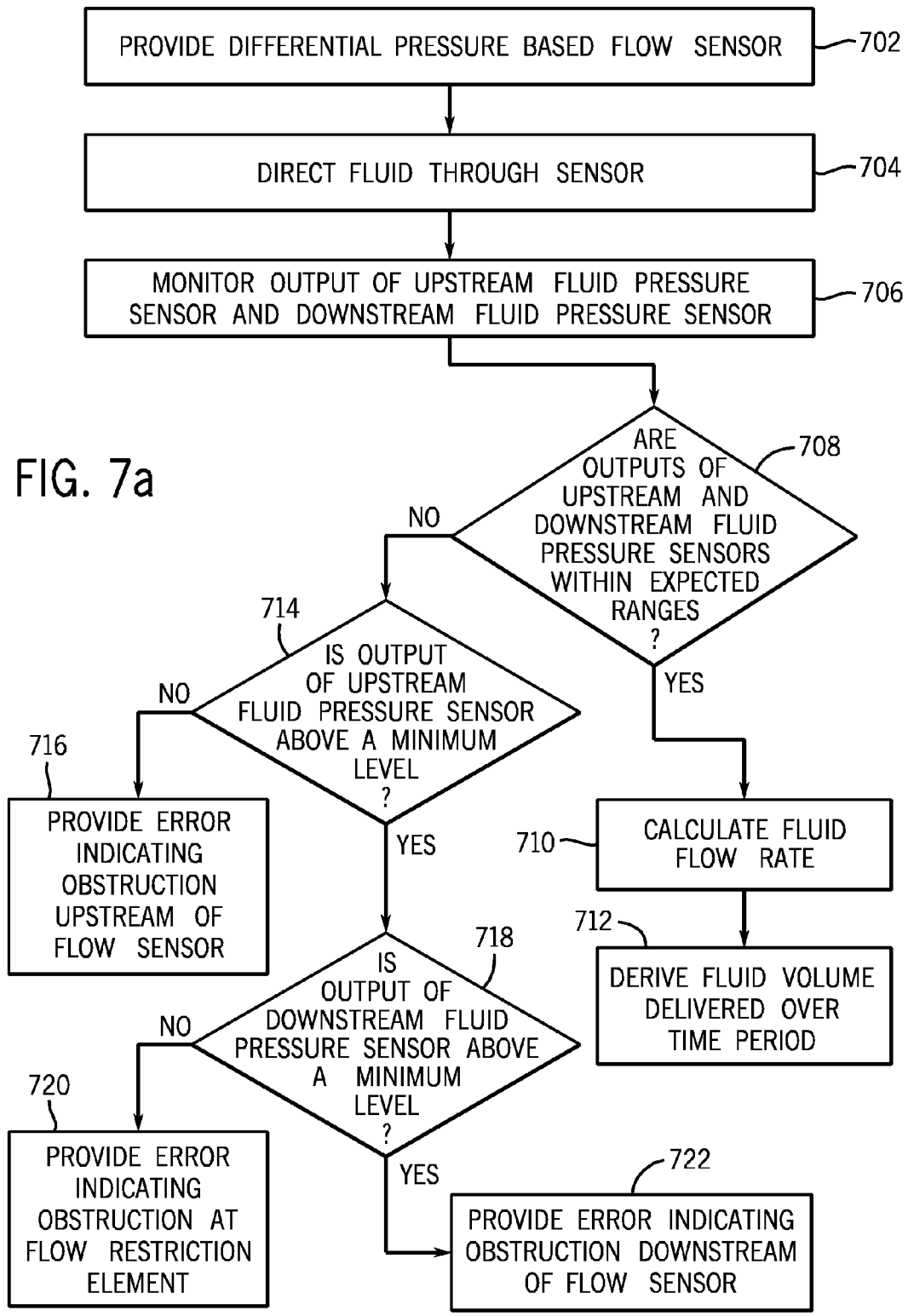
FIG. 7a schematically illustrates a method of delivering medication using a system with a differential pressure based flow sensor assembly, according to a more elaborate process than FIG. 7.

Turning now to FIG. 7a, a process of utilizing a differential pressure based sensor assembly to deliver a fluid is depicted, including monitoring for possible occlusions within the delivery system. The process provides a differential pressure based flow sensor in step 702. Fluid flows through the sensor in step 704 and the output of both the upstream fluid pressure sensor and the downstream fluid pressure sensor are monitored in step 706. The process determines whether the outputs of both the upstream fluid pressure sensor and the downstream fluid pressure sensor are within expected ranges in step 708. If so, the process calculates the fluid flow rate, utilizing the algorithm previously described, in step 710. Once the flow rate has been determined, the process derives the volume that has passed through the sensor assembly 100 over a given period of time in step 712. As described above with respect to FIG. 7, the sensor signals or measurements, timestamp information, differential pressure, flow rate and/or volume delivered are communicated to a memory, which can be located in the sensor assembly 100, in the infusion pump 12, or another processor.

If the outputs of the upstream and downstream fluid pressure sensors do not fall within expected ranges, the process determines if the output of the upstream fluid pressure sensor is above a minimum level in step 714. If the pressure is not above a preset minimum level, an error signal is generated in step 716, indicating that a possible obstruction exists upstream of the differential pressure based flow sensor assembly 100. However, if the output of the upstream fluid pressure sensor is above a minimum level, the process in step 718 determines if the output level of the downstream fluid pressure sensor is above a preset minimum level. If the output of the downstream fluid pressure sensor is not above a preset minimum level, an error signal is generated in step 720 that indicates an obstruction may be present at the flow restricting element 112. However, if the downstream fluid pressure sensor detects a pressure above the preset minimum level, an error signal is generated in step 722 indicating that an obstruction may be present downstream of the differential pressure based flow sensor assembly 100.

Thus, utilizing the process illustrated in FIG. 7a, the flow rate of a fluid as well as the volume of the fluid delivered through a differential pressure based flow sensor assembly may be calculated, and an error message may be provided when an occlusion occurs.

Figure 8A:
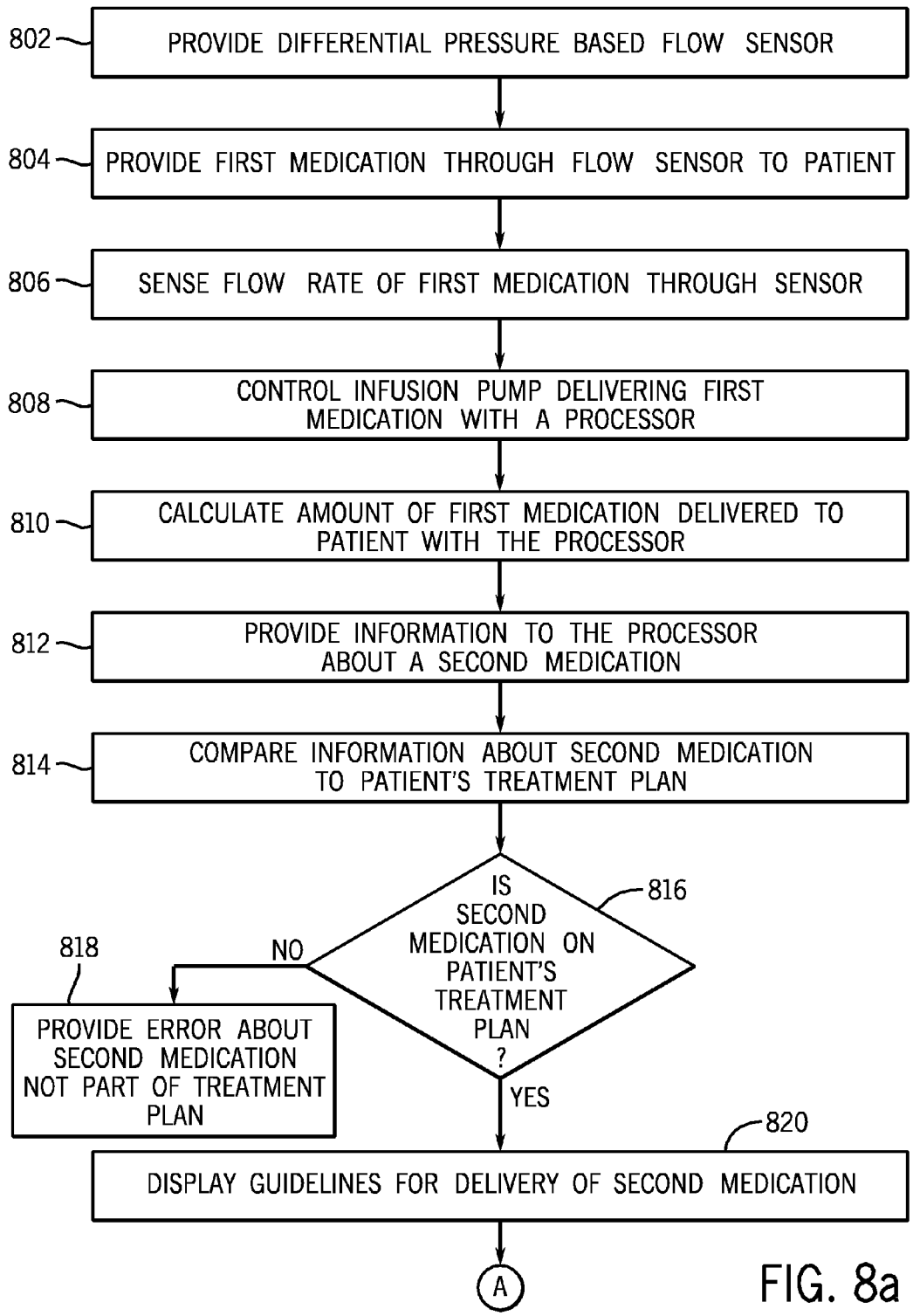
FIGS. 8a-8b schematically illustrate a method of delivering medication using a system having a differential pressure based flow sensor assembly according to another process.
Figure 8B:
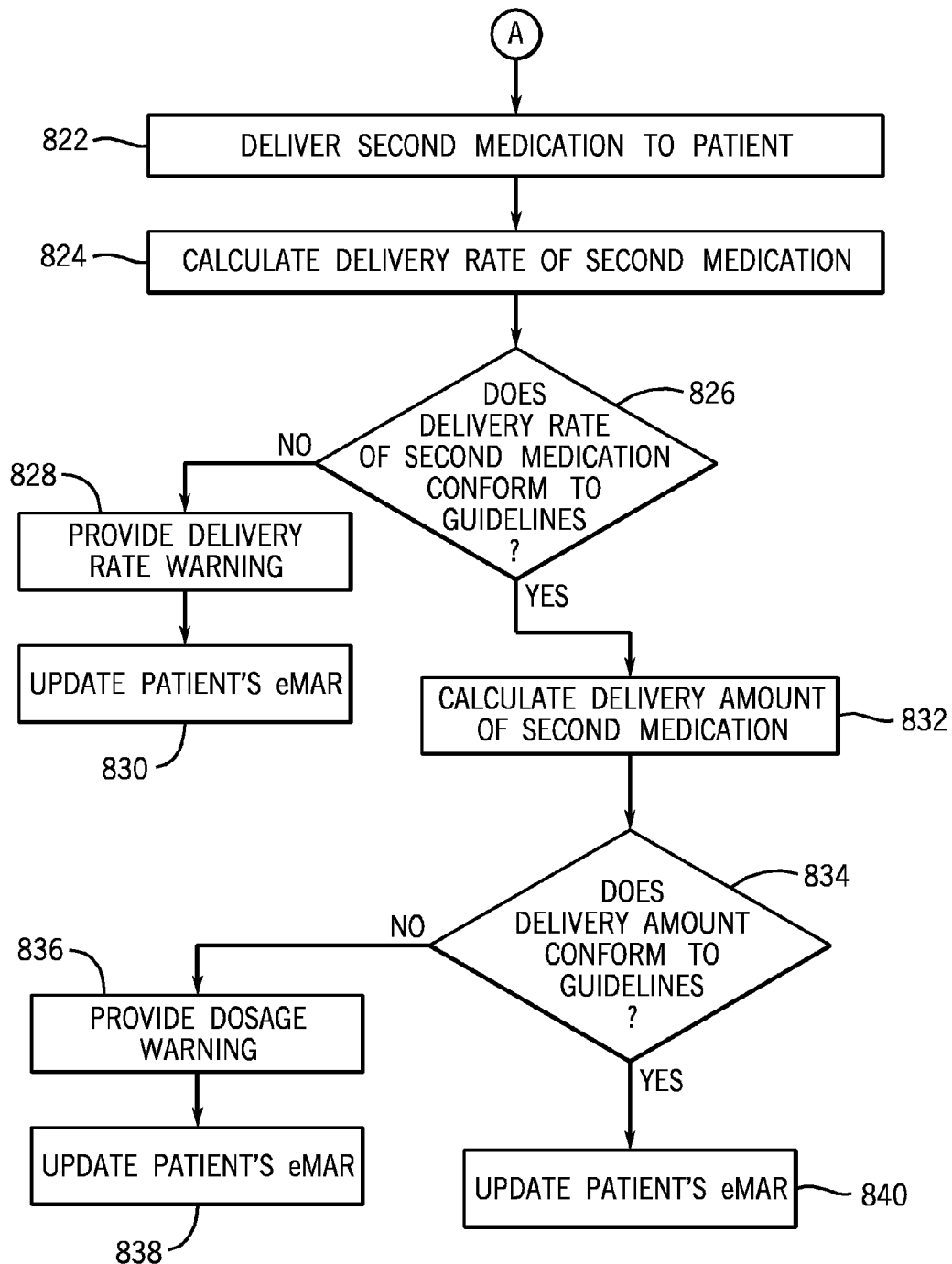

As shown in FIGS. 8a-8b, a method of delivering medication to a patient utilizing a medication delivery system having an infusion pump is depicted in block diagram form. The process provides a differential pressure based flow sensor assembly in step 802, such as sensor assembly 100 previously described herein. A first medication is provided through the flow sensor assembly to the patient 10 in step 804. The flow through the sensor assembly is sensed in step 806. In step 808, the process controls an infusion pump delivering the first medication via a processor. The amount or volume of the first medication delivered to the patient is calculated in step 810 using the processor and signals received from the differential pressure based flow sensor assembly 100. Information about a second medication to be delivered to the patient is provided to the processor in step 812. The information provided about the second medication is compared to information within the patent's treatment plan in step 814. The process determines in step 816 whether the second medication is on the patient's specific treatment plan, such as by checking whether the patient has a medical order or prescription for the second medication. If the second medication is not found on the patient's treatment plan, an error message is provided in step 818 indicating that the second medication is not found on the patient's treatment plan, and the caregiver should check with a physician or other caregiver to determine if it is appropriate to provide the second medication to the patient. If the second medication is found on the patient's treatment plan, guidelines for delivering the second medication are generated or displayed in step 820. The guidelines can include but are not limited to a target delivery rate with upper and/or lower limits, a total volume or amount to be delivered during the bolus, and a time period over which to deliver the IV push or bolus.

Continuing now to FIG. 8b, the second medication is delivered to the patient in step 822. The process calculates the delivery rate of the second medication using the differential pressure based flow rate sensor assembly 100 in step 824. As described with respect to FIG. 7 above, the delivery flow rate calculations can be stored in memory. A comparison is performed in step 826 to determine if the delivery rate of the second medication conforms to the delivery guidelines. If the delivery rate does not conform to the delivery guidelines, a delivery rate warning is provided to the caregiver in step 828. If the delivery rate warning is provided, the patient's electronic medication administration record (eMAR) is updated in step 830 to show that the second medication was delivered at a rate inconsistent with the delivery guidelines or protocols. The amount of the second medication delivered to the patient can also be calculated in step 832. The process in step 834 compares the amount of the second medication delivered to the amount of the second medication the patient was scheduled to receive. If the amount of the second medication the patient received does not conform to the patient's treatment plan, a dosage warning is provided to the caregiver at step 836. This warning can indicate that the patient was provided an underdose of the second medication, or that the patient was provided with an overdose of the second medication. The patient's electronic medication administration record (eMAR) is updated in step 838 to include the amount of the second medication that was provided to the patient, as well as information to indicate that the dosage of the second medication did not conform to the patient's treatment plan. If the amount of the second medication delivered to the patient conforms to the patient specific guidelines, the patient's electronic medication administration record (eMAR) is updated in step 840 to indicate that a proper dosage of the second medication was delivered to the patient. It is contemplated that every update to the patient's electronic medication administration record (eMAR) will note the time a medication was delivered to the patient, as well as the caregiver responsible for delivering that medication to the patient.

According to a further embodiment, a disposable infusion tubing set is provided that has a disposable portion of a differential pressure based flow sensor assembly. The tubing set would include at least a first tube adapted to connect to a first medication reservoir, and a connection site to allow a second medication to be introduced into the first tube of the tubing set upstream of the disposable portion of the differential pressure based flow sensor assembly. The disposable infusion tubing set further has a second tube adapted to connect to a patient access device. The second tube is adapted to be positioned downstream of the disposable portion of the differential pressure based flow sensor assembly. As discussed above, the disposable portion of the differential pressure based flow sensor assembly can be disposed in other locations within the disposable infusion tubing set, depending on the line pressure conditions, delivery flow rates, or fluid volume delivery amounts of interest.

According to yet another embodiment, a differential pressure based flow rate sensor assembly is replaced by a pressure based event detection sensor. A pressure based event detection sensor allows an event, such as a bolus, to be detected noting a spike in pressure. Such an event detection sensor would not allow the computation of the volume of medication delivered, but will place a notation onto a patient's record that some medication was delivered at a specific time. Thus, a record will exist confirming that a patient was provided with medication.

According to yet a further embodiment, a differential pressure based flow sensor assembly may be powered by an inductive power source. Such an embodiment would contain many of the same features as the differential pressure based flow sensor assembly 100 described herein. Similarly, it is contemplated that a wireless differential pressure based flow sensor assembly may transmit information regarding a pressure at an upstream pressure sensor and information regarding a downstream pressure sensor to other components within a system. Finally, it is contemplated that the portion 104 of the differential pressure based flow sensor assembly 100 could be produced using MEMS, integrated circuits or other technology in a miniaturized and low cost manner, such that the portion 104 might be considered disposable as well.

Figure 9:
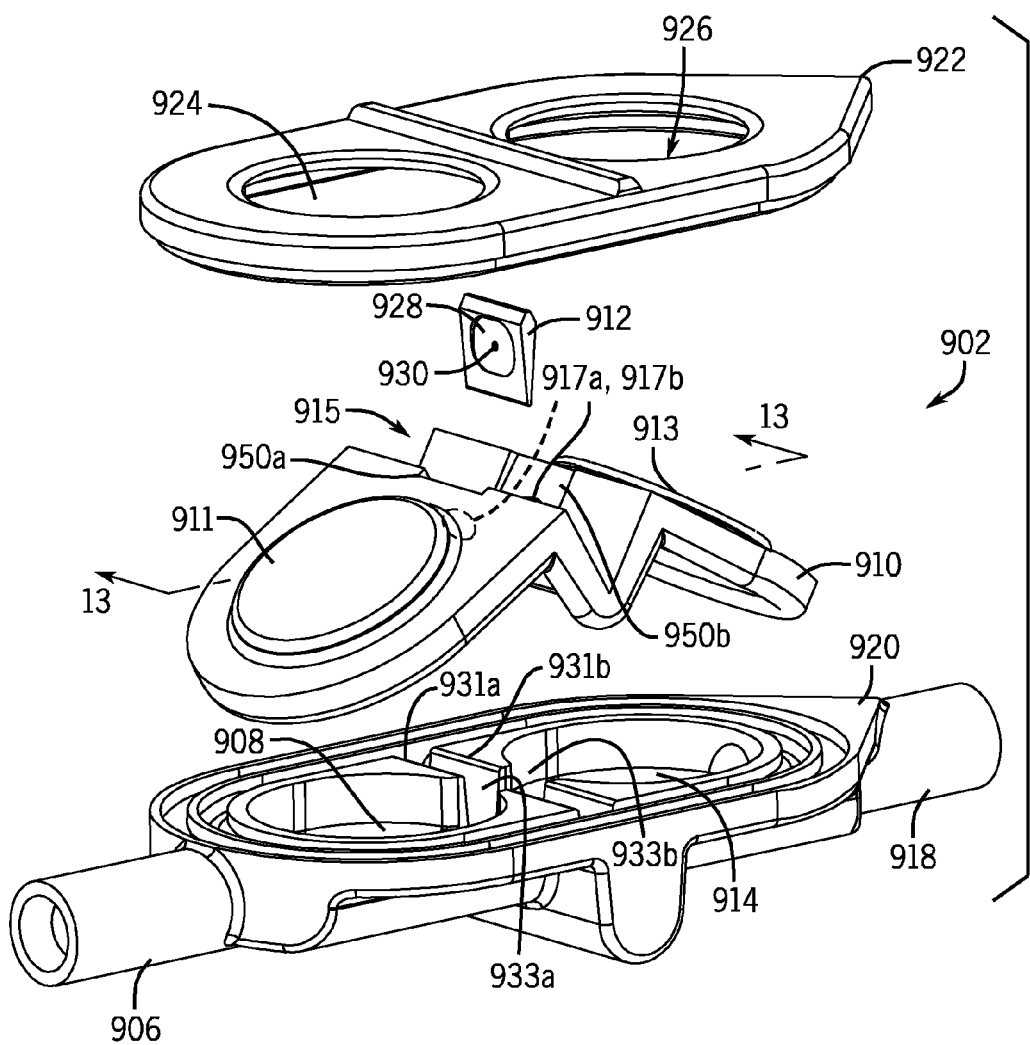
FIG. 9 is an exploded pictorial view of a disposable portion of a differential pressure based flow sensor assembly according to another embodiment.

Turning next to FIG. 9, another alternative embodiment of a disposable portion 902 for a differential pressure based flow sensor assembly 900 (FIGS. 10 and 11) is depicted. The disposable portion 902 comprises: a fluid inlet 906; an upstream fluid chamber 908; a fluid pressure membrane 910; a flow restricting element 912; a downstream fluid chamber 914; and a fluid outlet 918. The membrane 910 is generally fluid impermeable, except as described below. The disposable portion 902 has a base 920 and a lid 922.

As shown in FIG. 9, medication, or some other fluid, enters the disposable portion 902 through the fluid inlet 906. The medication flows into the upstream fluid chamber 908 from the fluid inlet 906. Next, the medication flows through the flow restricting element 912 and into the downstream fluid chamber 914. The flow of the medication through the flow restricting element 912 results in a drop in fluid pressure as the fluid flows from the upstream fluid chamber 908 to the downstream fluid chamber 914 through the flow restricting element 912. Thus, during forward fluid flow under normal conditions, the fluid pressure within the upstream fluid chamber 908 is generally greater the fluid pressure within the downstream fluid chamber 914. The fluid pressure membrane 910 is disposed along the fluid flow passage between the inlet 906 and the outlet 918. The fluid pressure membrane 910 basically defines a wall of the fluid flow passage. The fluid pressure within the upstream fluid chamber 908 presses against a first area 911 of the fluid pressure membrane 910. Similarly, the fluid pressure within the downstream fluid chamber 914 presses against a second area 913 of the fluid pressure membrane 910.

The lid 922 forms an upstream opening 924 and a downstream opening 926 to allow the first and second areas 911, 913 of the fluid pressure membrane 910 to communicate, respectively, with the upstream pressure sensor 120 and the downstream pressure sensor 122 of the reusable portion 104. The first and second areas 911, 913 may be raised to extend into or more preferably through the openings 924, 926 to engage the sensors 120, 122. Raising the first and second areas 911, 913 additionally aids in the positioning of the lid 922 and the membrane 910 during assembly.

Figure 12:
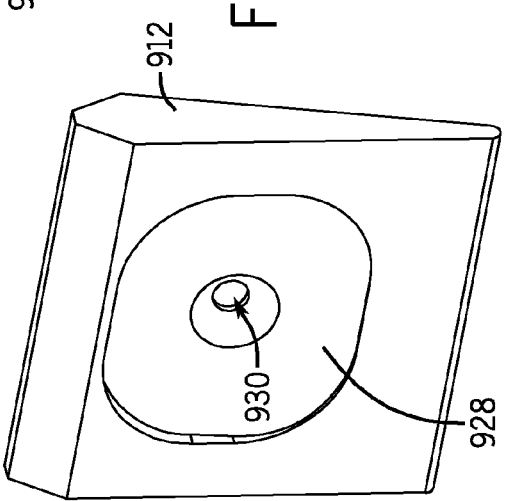
FIG. 12 is a pictorial view of one embodiment of a flow restricting element adapted to be used with the disposable portion of FIG. 9.

As shown in FIG. 9, the fluid pressure membrane 910 is a flexible diaphragm type membrane. The fluid pressure membrane 910 may be formed from silicone, or some other flexible polymeric material or elastomeric material. In FIG. 9, the membrane 910 forms or has a flange, such as by a fold or the original molded shape, that extends into the fluid flow passage. The flange or fold defines an opening 915 for receiving the flow restricting element 912. The opening 915 is disposed between the first and second areas 911, 913 of the membrane 910. Apertures 917a, 917b respectively extend through opposing sidewalls of the opening 915. The flow restricting element 912 is adapted to be placed within the opening 915 of the fluid pressure membrane 910. As more clearly shown in FIG. 12, the flow restricting element 912 has an opening 930 formed therethrough and optionally has a recessed surface 928 formed therein around the opening 930 on one or both of the upstream and downstream sides. The opening 930 causes a pressure drop to occur as fluid flows through the opening 930, allowing the flow rate of the fluid to be determined as previously described. In the embodiment shown in FIG. 9 the flow restricting element is a wedge shaped plate.

Once the flow restricting element 912 is placed within the receiving opening 915 of the fluid pressure membrane 910, the membrane 910 may be placed within the base 920. The membrane 910 may be folded or compressed, so as to contract the opening 915 and fully surround the flow restricting element 912. The base 920 can include at least one upright guide, and more preferably a pair of spaced apart upright guides 931a, 931b, for receiving, guiding, supporting, and/or compressing the portion of the membrane 910 that includes the flow restricting element receiving opening 915. The guides 931a, 931b include apertures 933a, 933b respectively that are in communication with the apertures 917a, 917b of the membrane and the opening 930 of the flow restricting element 912 in the assembled state. The lid 922 is positioned such that the fluid pressure membrane 910 is positioned between the base 920 and the lid 922. The lid 922 and the base 920 may be ultrasonically welded together to form a fully assembled disposable portion 902, as viewed in FIG. 10. The fluid pressure membrane 910 may thus be firmly secured between the base 920 and the lid 922 without the use of any adhesive to fasten the fluid pressure membrane 910 to either the base 920 or the lid 922. Eliminating the need to fasten the fluid pressure membrane 910 to either the base 920 or the lid 922 simplifies the manufacturing of the disposable portion 902. The flow restricting element is also secured in a fluidly sealed manner in proper position along the fluid flow path without the need for fasteners, adhesives, or elaborate machining and assembly techniques.

At least one of the opposing sidewalls of the opening 915 of the fluid pressure membrane 910 optionally has a slot or recess 950a, 950b, 932 formed therein for receiving the flow restricting element 912. More preferably both of the sidewalls include slots or recesses 950a, 950b, 932 sized, shaped and positioned so as to receive, position and orient the flow restricting element 912. When the membrane 910 is folded or compressed, so as to contract the opening 915, the slots or recesses 950a, 950b, 932 can be adapted to fully surround the flow restricting element 912. The slots 950a, 950b assist in positioning the flow restricting element 912 relative to the apertures 917a, 917b to help ensure proper fluid flow through the disposable portion 902. The slots or recesses also assist in forming a seal around the flow restricting element 912.

Figure 13:
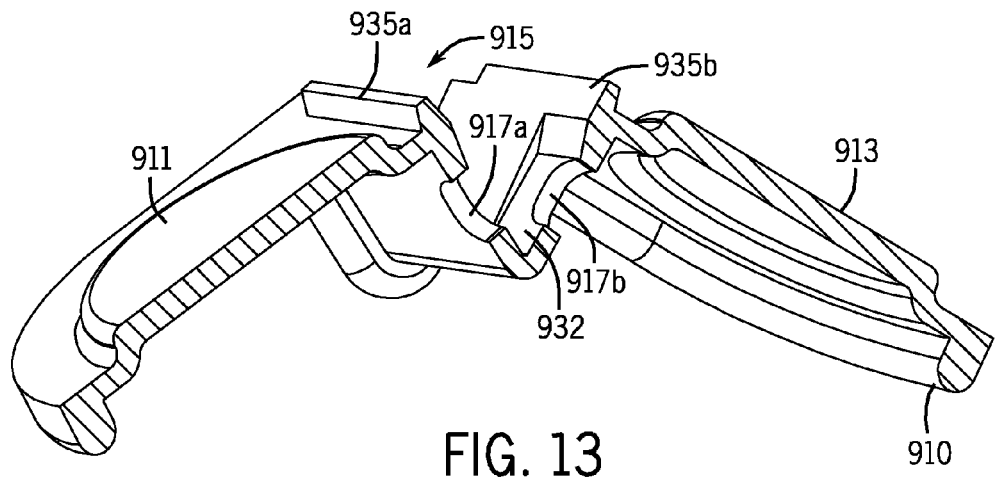
FIG. 13 is a cross-sectional view of a fluid pressure membrane taken along line 13-13 of FIG. 9.

A more detailed cross sectional view of one embodiment of the fluid pressure membrane 910 may be observed in FIG. 13. One or more of the opposing sides of the membrane 910 at the opening 915 has a recess 932 formed therein to receive the flow restricting element 912. The recess 932 is in communication with the apertures 917a, 917b to allow fluid to flow through the membrane 910 and the flow restricting element 912. The recess 932 provides positioning (including both alignment and orientation) for the flow restricting element 912. The recess 932 also enhances the ability of the resilient flexible membrane to create an effective fluid seal around the flow restricting element. The fluid pressure membrane 910 further has a first rib 935a located on one side of the opening 915 and a second rib 935b located on an opposite side of the opening 915 as the first rib 935a. The ribs 935a, 935b come together when the membrane 910 is folded or compressed so as to contract the opening 915. The ribs 935a, 935b are adapted to assist in positioning the fluid pressure membrane 910 relative to the lid 922. The lid 922 may have a recess (not shown) adapted to receive the ribs 935a, 935b so as to limit the ability of the membrane 910 to move relative to the lid 922 during assembly of the disposable portion 902.

Figure 10:
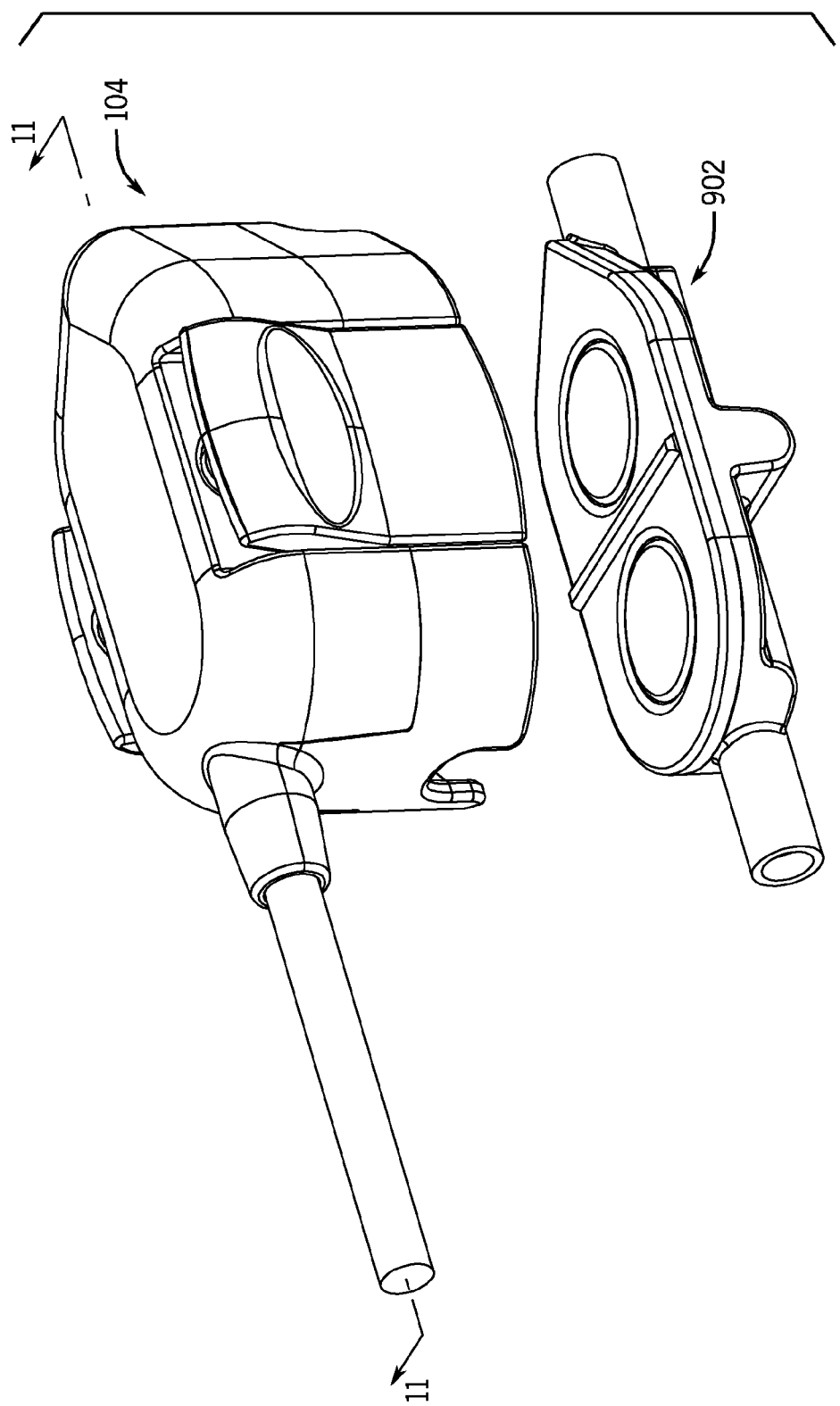
FIG. 10 is an exploded pictorial view of a differential pressure based flow sensor assembly having the disposable portion of FIG. 9.
Figure 11:
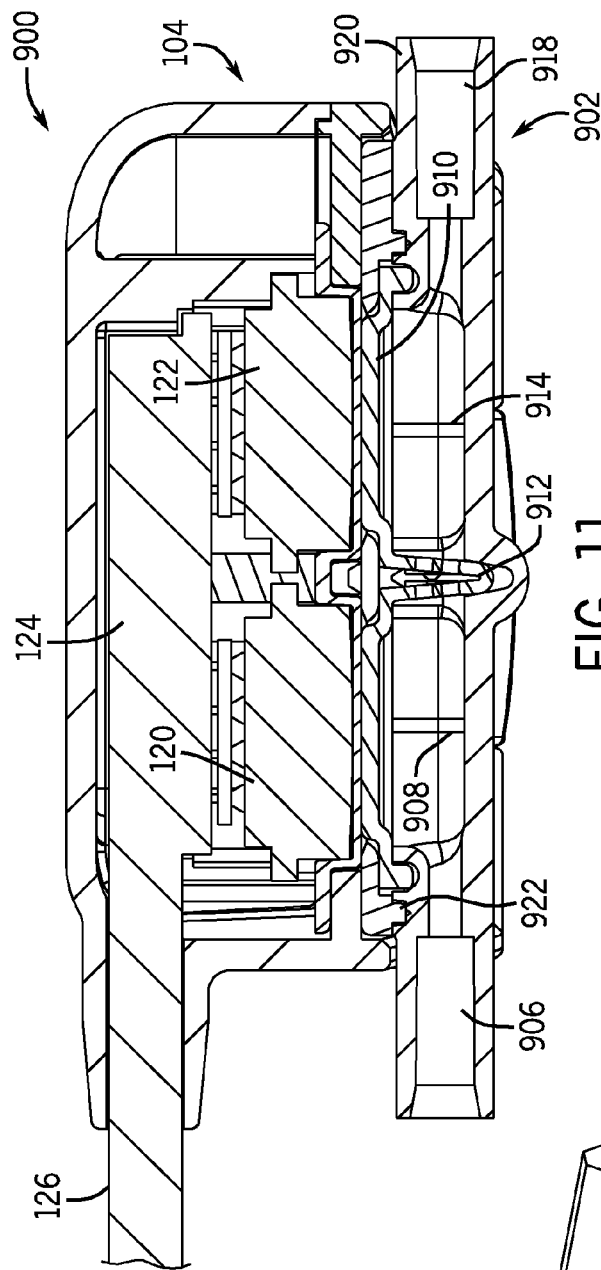
FIG. 11 is a cross-sectional view taken along line 11-11 of FIG. 10.

Turning now to FIGS. 10 and 11, the relationship of the disposable portion 902 and the reusable portion 104 are shown, including the formation of the differential pressure based flow rate sensor assembly 900 (FIG. 11). The disposable portion 902 cooperates with the reusable portion 104 in a manner generally identical to that previously described above.

As shown in FIG. 11, medication enters the disposable portion 902 through the fluid inlet 906. The medication flows into the upstream fluid chamber 908 from the fluid inlet 906. Next, the medication flows through the flow restricting element 912 and into the downstream fluid chamber 914. The flow of the medication through the flow restricting element 912 results in a drop in fluid pressure as the fluid flows from the upstream fluid chamber 908 to the downstream fluid chamber 914 through the flow restricting element 912. Thus, during forward fluid flow under normal conditions, the fluid pressure within the upstream fluid chamber 908 is generally greater the fluid pressure within the downstream fluid chamber 914. The fluid pressure within the upstream fluid chamber 908 presses against the fluid pressure membrane 910, causing the membrane 910 to pass through the upstream opening 924 of the lid 922 to press against the upstream fluid pressure sensor 120. Similarly, the fluid pressure within the downstream fluid chamber 914 presses against the fluid pressure membrane 910, causing the membrane 910 to pass through the downstream opening 926 of the lid 922 to press against the downstream fluid pressure sensor 122.

It is contemplated that a variety of materials may be utilized for the manufacture of the disposable portion 902. The disposable portion 902 may comprise a thermoplastic. It is contemplated that the flow restricting element 912 may be made of the same thermoplastic as the rest of the disposable portion 902, or may be a different material than the disposable portion 902. Non-limiting examples of the material that may be utilized to form the flow restricting element 912 include silicon, glass, and medical grade thermoplastics and elastomers. The flow restricting element 912 even can be made in whole or in part of stainless steel. A stainless steel orifice plate can be encased in a thermoplastic or elastomeric frame. The fluid pressure membranes 910 may comprise a variety of polymeric or elastomeric materials, such as TPE, or silicone.

As previously described in connection with FIG. 4, the reusable portion 104 of the differential pressure based flow rate sensor assembly 900 uses the circuit board 124 to calculate pressure difference between the upstream fluid chamber 908 and the downstream fluid pressure chamber 914 based on signals received from the respective pressure sensors 120, 122, or the circuit board 124 may generate an output signal that is transmitted to another device with a processor, such as the infusion pump 12, that calculates the pressure difference between the upstream chamber 908 and the downstream chamber 914. Output of the circuit board 124 passes through electrical connection 126 to the infusion pump 12 (FIG. 1).

Figure 14:
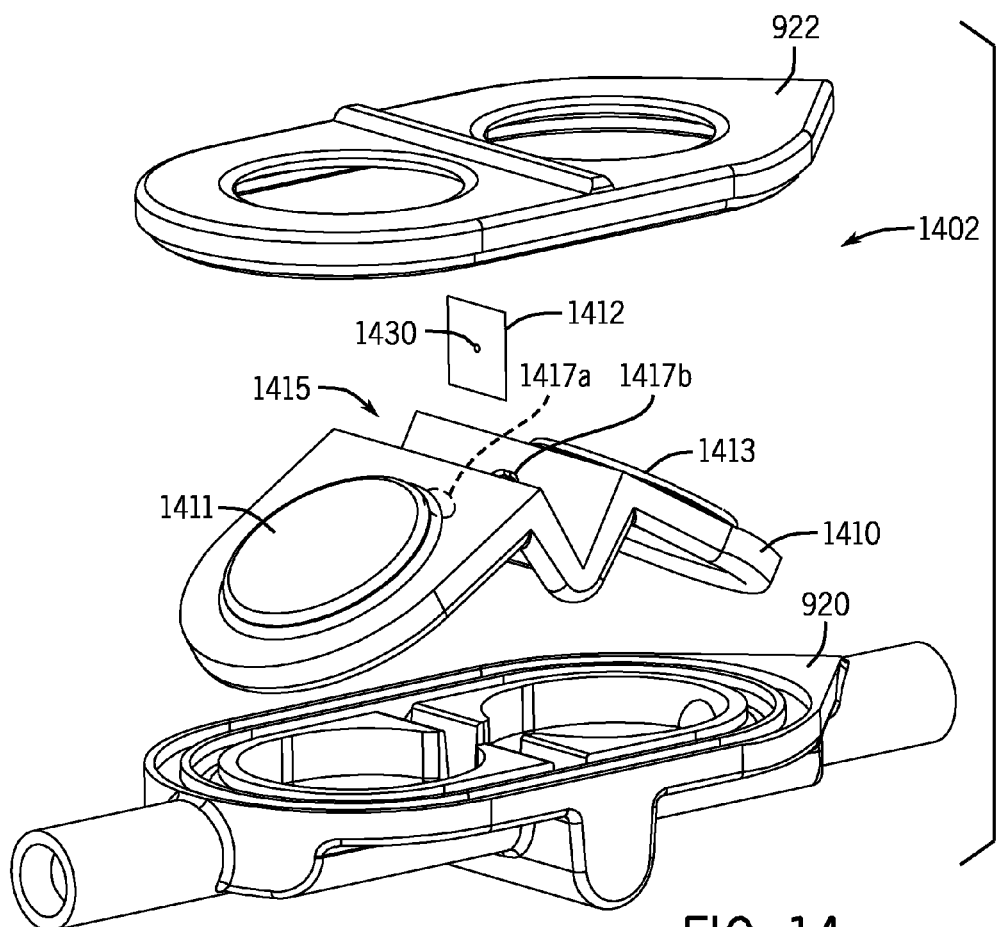
FIG. 14 is an exploded pictorial view of a disposable portion of a differential pressure based flow sensor assembly according to still yet another embodiment.

FIG. 14 shows a further alternative embodiment of a disposable portion 1402. The disposable portion 1402 is very similar to the disposable portion 902 shown in FIG. 9. In fact, it is contemplated that only a fluid pressure membrane 1410 and a flow restricting element 1412 of disposable portion 1402 differs from the disposable portion 902. As the other components of the disposable portion 1402 are identical to those of the disposable portion 902, the description previously provided above in connection to FIG. 9 is applicable to those components.

The fluid pressure membrane 1410 is a flexible diaphragm type membrane. The fluid pressure membrane 1410 may be formed from silicone, or some other flexible polymeric material or elastomeric material. The membrane 1410 forms or has a flange, such as by a fold or the original mold shape, that defines an opening 1415 for receiving the flow restricting element 1412. The flow restricting element has an opening 1430. The opening 1430 causes a pressure drop to occur as fluid flows through the opening 1430, allowing the flow rate of the fluid to be determined as previously described. The opening 1415 of the membrane 1410 is disposed between first and second areas 1411, 1413 of the membrane 1410. Apertures 1417a, 1417b respectively extend through opposing sidewalls of the opening 1415. The opening 1415 is sized and positioned so as to receive and surround the flow restricting element 1412 when the membrane 1410 is folded or compressed, so as to contract the opening 1415. Thus, opening 1415 fully surrounds the flow restricting element 1412 when the membrane 1410 is folded or compressed. The flow restricting element 1412 may be a thin plate, such as a stainless steel plate, although other materials may also be used. The flow restricting element 1412 is preferably substantially flat or planar in one embodiment. The thinness of the flow restricting element 1412 assists in forming a fluid tight seal between the membrane 1410 and the flow restricting element 1412 when the membrane 1410 is folded or compressed to contract the opening 1415. The flow restricting element 1412 is so thin that no slot or recess is required near the opening 1415 of the membrane 1410 to assist in forming a seal around the flow restricting element 1412.

It is contemplated that the opening 915 or fold in the fluid pressure membrane 910 can be inverted and receive the flow restricting element 912. It is also contemplated that a slot or opening 915 can be provided in the base portion 920 or in both the base portion and the membrane 910 for receiving the flow restricting element 912.

While the foregoing has described what is considered to be the best mode and/or other examples, it is understood that various modifications may be made and that the subject matter disclosed herein may be implemented in various forms and examples, and that they may be applied in numerous other applications, combinations and environments, only some of which have been described herein. Those of ordinary skill in that art will recognize that the disclosed aspects may be altered or amended without departing from the true scope of the subject matter. Therefore, the subject matter is not limited to the specific details, exhibits and illustrated examples in this description. It is intended to protect any and all modifications and variations that fall within the true scope of the advantageous concepts disclosed herein.

We claim:

1. A differential pressure based flow sensor assembly to determine the flow rate of a fluid system comprising:
    a disposable portion having:
        a body defining a fluid flow passage forming an inlet and an outlet, the body having a base portion and a lid portion;
        a flexible fluid pressure membrane disposed along the fluid flow passage between the inlet and the outlet, the fluid pressure membrane being secured between the base portion and the lid portion of the body; and
        a flow restricting element positioned in the fluid flow passage between the inlet and the outlet;
        wherein lid portion has a first opening and a second opening, and the fluid pressure membrane has a first area and a second area adapted to be aligned with the first opening and the second opening respectively of the lid portion;
        wherein the fluid pressure membrane defines an opening between the first area and the second area for receiving the flow restricting element; and
    a reusable portion having:
        an upstream fluid pressure sensor disposed outside the fluid flow passage and adapted to be pressed upon by the first area of the fluid pressure membrane through the first opening of the lid portion in order to sense an upstream fluid pressure at an upstream location in the fluid flow passage between the inlet and the flow restricting element; and
        a downstream fluid pressure sensor disposed outside the fluid flow passage and adapted to be pressed upon by the second area of the fluid pressure membrane through the second opening of the lid portion in order to sense a downstream fluid pressure at a downstream location in the fluid flow passage between the flow restricting element and the outlet.

2. The differential pressure based flow sensor assembly of claim 1, wherein the fluid pressure membrane further has a rib adapted to assist in positioning the fluid pressure membrane relative to the lid portion.

3. The differential pressure based flow sensor assembly of claim 1, wherein the base portion has at least one upright guide adapted to interact with the flexible membrane to assist in positioning the flexible membrane relative to the base portion.

4. The differential pressure based flow sensor assembly of claim 3, wherein the at least one upright guide comprises a pair of spaced upright guides that further assists in compressing the flexible membrane to secure the flow restricting element within the opening of the flexible membrane.

5. The differential pressure based flow sensor assembly of claim 1, wherein the flow restricting element is a non-capillary fluid flow path.

6. The differential pressure based flow sensor assembly of claim 5, wherein the flow restricting element is an orifice.

7. The differential pressure based flow sensor assembly of claim 6, wherein a perimeter of an opening of the orifice is larger than a length of a path the fluid travels through the orifice.

8. The differential pressure based flow sensor assembly of claim 7, wherein a ratio of the perimeter to the length of the path the fluid travels through the orifice is about 1000:1.

9. The differential pressure based flow sensor assembly of claim 1, wherein the flow restricting element is a separate component from the lid portion and the base portion and is secured within the fluid pressure membrane.

10. The differential pressure based flow sensor assembly of claim 1, wherein the fluid pressure membrane defines a wall of the fluid flow passage and has a flange that extends into the fluid flow passage between the base portion and the lid portion of the body of the disposable portion, the opening for receiving the flow restricting element being formed in the flange of the fluid pressure membrane.

11. The differential pressure based flow sensor assembly of claim 10, wherein the flange is defined by a fold in the fluid pressure membrane and the opening for receiving the flow restricting element is formed in the fold.

12. A disposable assembly for use with a differential pressure based fluid flow sensor assembly, the disposable assembly comprising:
 a body having a lid portion secured to a base portion, the body defining a fluid flow passage forming an inlet and an outlet, the lid portion having a first opening and a second opening;
 a flow restricting element positioned in the fluid flow passage between the inlet and the outlet; and
 a flexible fluid pressure membrane disposed along the fluid flow passage between the inlet and the outlet and secured between the base portion and the lid portion of the body, the fluid pressure membrane defining an opening for receiving the flow restricting element, the opening for receiving the flow restricting element being located between a first area of the membrane that is aligned with the first opening of the lid portion and a second area of the membrane that is aligned with the second opening of the lid portion.

13. The disposable assembly of claim 12, wherein the flow restricting element has an orifice and the opening for receiving the flow restricting element is defined by opposing side walls formed by the fluid pressure membrane and each of the side walls has an aperture extending therethrough so as to provide fluid communication with the orifice of the flow restricting element.

14. The disposable assembly of claim 13, wherein the opposing side walls are defined by a fold in the fluid pressure membrane.

15. The disposable assembly of claim 13, wherein at least one of the opposing side walls has a recess formed therein for receiving and positioning the flow restricting element.

16. The disposable assembly of claim 13, wherein both of the opposing side walls have a recess formed therein for receiving and positioning the flow restricting element.

17. The disposable assembly of claim 12, wherein the base portion has at least one pair of upright guides adapted to interact with the fluid pressure membrane to assist in positioning the flexible membrane relative to the base portion.

18. The disposable assembly of claim 12, wherein the flow restricting element is a wedge shaped plate.

19. The disposable assembly of claim 12, wherein the flow restricting element is a separate component secured within the fluid pressure membrane.

20. The disposable assembly of claim 12, wherein the fluid pressure membrane defines a wall of the fluid flow passage and has a flange that extends into the fluid flow passage between the lid portion and the base portion of the body, the opening for receiving the flow restricting element being formed in the flange of the fluid pressure membrane.

21. The disposable assembly of claim 20, wherein the lid portion is ultrasonically welded to the base portion.

22. A method of forming a disposable flow sensor assembly comprising the steps of:
 providing a base portion, a lid portion, a flow restricting element and a flexible fluid pressure membrane;
 forming an opening in the fluid pressure membrane for receiving the flow restricting element;
 inserting the flow restricting element into the opening;
 positioning the fluid pressure membrane and the flow restricting element between the base portion and the lid portion; and
 securing the lid portion to the base portion.

23. The method of claim 22, wherein the securing the lid portion to the base portion secures the fluid pressure membrane between the base portion and the lid portion.

24. The method of claim 22, further comprising forming a pair of apertures in the fluid pressure membrane in fluid communication with the opening and the flow restricting element so as to provide fluid communication through the fluid pressure membrane and the flow restricting element.

25. The method of claim 22, wherein the forming of the opening in the fluid pressure membrane includes folding the fluid pressure membrane so as to define a fold that receives the flow restricting element.

26. The method of claim 25, wherein the fold defines opposing sides walls and the method further comprises forming a recess in one of the opposing side walls for receiving and positioning the flow restricting element.

27. The method of claim 25, wherein the fold defines opposing sides walls and the method further comprises forming a recess in each of the opposing side walls for receiving and positioning the flow restricting element.

28. The method of claim 26, wherein the recess of the fluid pressure membrane surrounds the flow restricting element.

29. The method of claim 22, further comprising forming a slot in the base portion for receiving the flow restricting element.

* * * * *